United States Patent
Dugan

(10) Patent No.: US 9,918,673 B2
(45) Date of Patent: *Mar. 20, 2018

(54) SYSTEMS, DEVICES, AND METHODS FOR TRACKING ABDOMINAL ORIENTATION AND ACTIVITY

(71) Applicant: Stephen Dugan, San Francisco, CA (US)

(72) Inventor: Stephen Dugan, San Francisco, CA (US)

(73) Assignee: Smart Human Dynamics, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/663,453

(22) Filed: Mar. 20, 2015

(65) Prior Publication Data

US 2015/0289822 A1 Oct. 15, 2015

Related U.S. Application Data

(63) Continuation of application No. 14/625,965, filed on Feb. 19, 2015, now Pat. No. 9,585,614.

(Continued)

(51) Int. Cl.
*A61B 5/00* (2006.01)
*A61B 5/11* (2006.01)
(Continued)

(52) U.S. Cl.
CPC .......... *A61B 5/4343* (2013.01); *A61B 5/0077* (2013.01); *A61B 5/021* (2013.01);
(Continued)

(58) Field of Classification Search
CPC ... A61B 2503/02; A61B 5/0077; A61B 5/021; A61B 5/08; A61B 5/1072; A61B 5/1073;
(Continued)

(56) References Cited

U.S. PATENT DOCUMENTS 5,938,626 A  8/1999  Sugerman
6,095,991 A  8/2000  Krausman
(Continued)

FOREIGN PATENT DOCUMENTS

WO  WO 2005067796 A1  7/2005
WO  WO 2010099764 A2  9/2010

OTHER PUBLICATIONS

Facco et al., "Abstracts LB1 and LB2", Feb. 6, 2015.
(Continued)

*Primary Examiner* — George Manuel
(74) *Attorney, Agent, or Firm* — Davis, Brown, Koehn, Shors & Roberts, P.C.

(57) ABSTRACT

The various embodiments herein relate to systems, devices, and methods for tracking abdominal orientation and activity for purposes of preventing or treating conditions of pregnancy or other types of medical conditions. In certain specific embodiments, the system, device, or method relates to identifying abdominal orientation risk values, calculating and updating a cumulative risk value, comparing the cumulative risk value to a threshold, and outputting a warning when the cumulative risk value crosses the threshold.

17 Claims, 10 Drawing Sheets

Related U.S. Application Data

(60) Provisional application No. 61/971,438, filed on Mar. 27, 2014, provisional application No. 61/986,665, filed on Apr. 30, 2014, provisional application No. 62/022,060, filed on Jul. 8, 2014, provisional application No. 62/059,557, filed on Oct. 3, 2014, provisional application No. 62/111,427, filed on Feb. 3, 2015.

(51) Int. Cl.
*A61B 5/021* (2006.01)
*A61B 5/08* (2006.01)
*A61B 5/107* (2006.01)
*A61B 5/145* (2006.01)
*A61B 5/1455* (2006.01)

(52) U.S. Cl.
CPC .............. *A61B 5/08* (2013.01); *A61B 5/1072* (2013.01); *A61B 5/1073* (2013.01); *A61B 5/1075* (2013.01); *A61B 5/1114* (2013.01); *A61B 5/1116* (2013.01); *A61B 5/4362* (2013.01); *A61B 5/6823* (2013.01); *A61B 5/6831* (2013.01); *A61B 5/7275* (2013.01); *A61B 5/746* (2013.01); *A61B 5/1107* (2013.01); *A61B 5/1118* (2013.01); *A61B 5/1121* (2013.01); *A61B 5/14542* (2013.01); *A61B 5/14552* (2013.01); *A61B 5/6832* (2013.01); *A61B 2503/02* (2013.01)

(58) Field of Classification Search
CPC ... A61B 5/1075; A61B 5/1107; A61B 5/1114; A61B 5/1116; A61B 5/1118; A61B 5/1121; A61B 5/14542; A61B 5/14552; A61B 5/4343; A61B 5/4362; A61B 5/6823; A61B 5/6831; A61B 5/6832; A61B 5/727; A61B 5/746
See application file for complete search history.

(56) References Cited

U.S. PATENT DOCUMENTS

| | | | |
|---|---|---|---|
| 7,314,451 B2* | 1/2008 | Halperin | A61B 5/113 600/529 |
| 7,938,476 B2 | 5/2011 | Braunbeck et al. | |
| 8,587,439 B2 | 11/2013 | Levine et al. | |
| 8,643,494 B1 | 2/2014 | Trout | |
| 9,198,615 B2 | 12/2015 | Levendowski | |
| 2008/0221398 A1 | 9/2008 | Ronchi et al. | |
| 2012/0035508 A1 | 2/2012 | Van Leer | |
| 2012/0158437 A1 | 6/2012 | Little et al. | |
| 2012/0191038 A1* | 7/2012 | Gerber | A61B 5/1071 604/67 |
| 2013/0184611 A1 | 7/2013 | Nichols | |
| 2013/0211772 A1 | 8/2013 | Ross | |
| 2013/0237772 A1* | 9/2013 | Pisani | A61B 5/0002 600/301 |
| 2014/0128778 A1 | 5/2014 | Chan | |

OTHER PUBLICATIONS

Owusu et al., "Association of maternal sleep practices with preeclampsia, low birth weight, and stillbirth among Ghanaian women", "International Journal of Gynecology and Obstetrics", Jan. 1, 2013, pp. 261-265, vol. 121, Publisher: FIGO.

Stacey et al., "Association between maternal sleep practices and risk of late stillbirth: a case-control study", Jan. 1, 2011, pp. 1-6, Publisher: BMJ.

Xiong et al., "Association of preeclampsia with high birth weight for age", Jul. 1, 2000, pp. 148-155, vol. 183, No. 1, Publisher: AJOG.

Higuchi et al., "Effect of Lateral Tilt Angle on the Volume of the Abdominal Aorta and Inferior Vena Cava in Pregnant and Nonpregnant Women Determined by Magnetic Resonance Imaging", "Anesthesiology", Feb. 1, 2015, vol. 122, No. 2.

Drummond et al., "Effects of Posture on Limb Blood Flow in Late Pregnancy", "British Medical Journal", Jun. 15, 1974.

Lee et al., "Haemodynamic effects from aortocaval compression at different angles of lateral tilt in non-labouring term pregnant women", "British Journal of Anaesthesia", Jan. 1, 2012, pp. 950-956, vol. 109, No. 6.

Kanayama et al., "Hypolumbarlordosis a predisposing factor for preeclampsia", "European journal of obsetrics and gynecology", Jan. 1, 1997, Publisher: Elsevier.

Sharwood et al., "Hypotension in obstetric spinal anaesthesia: a lesson from pre-eclampsia", "British Journal of Anaesthesia", Mar. 3, 2009, vol. 102, No. 3.

Lisonkova et al., "Incidence of preeclampsia: risk factors and outcomes associated with earlyversus late-onset disease", Dec. 1, 2013, vol. 209, No. 6.

O'Brien et al., "Maternal sleep position: what do we know where do we go?", "BMC Pregnancy and Childbirth 2015", Jan. 1, 2015, vol. 15.

Chen et al., "Obstructive sleep apnea and the risk of adverse pregnancy outcomes", "American Journal of Obstetrics", Feb. 1, 2012, Publisher: AJOG.

Louis et al., "Perinatal Outcomes Associated With Obstructive Sleep Apnea in Obese Pregnant Women", "Obstet Gynecol", Nov. 1, 2012, vol. 120, No. 5, Publisher: NIH.

Bourjeily et al., "Pregnancy and fetal outcomes of symptoms of sleep disordered breathing", Jan. 1, 2010, vol. 36, No. 4, Publisher: ERS.

Li et al., "Presence of depressive symptoms during early pregnancy and the risk of preterm delivery: a prospective cohort study", "Human Reproduction", Jan. 1, 2009, pp. 146-153, vol. 24, No. 1.

Conde-Agudelo et al., "Risk factors for preeclampsia in a large cohort of Latin American and Caribbean women.", Jan. 1, 2000, pp. 75-83, vol. 107, No. 1.

Gordon et al., "Sleep Position, Fetal Growth Restriction, and Late-Pregnancy Stillbirth", "Obstetrics & Gynecology", Feb. 1, 2015, vol. 125, No. 2, Publisher: The American College of Obstetricians.

"Too much exercise in early pregnancy may cause preeclampsia", "Royal College of Obstetricians and Gynaecologists", Jan. 1, 2013, Publisher: RCOG.

Jeffreys et al., "Uterine blood flow during supine rest and exercise after 28 weeks of gestation", Jul. 19, 2006, Publisher: BJOG An International Journal of Obstetrics and Gynaecology.

\* cited by examiner

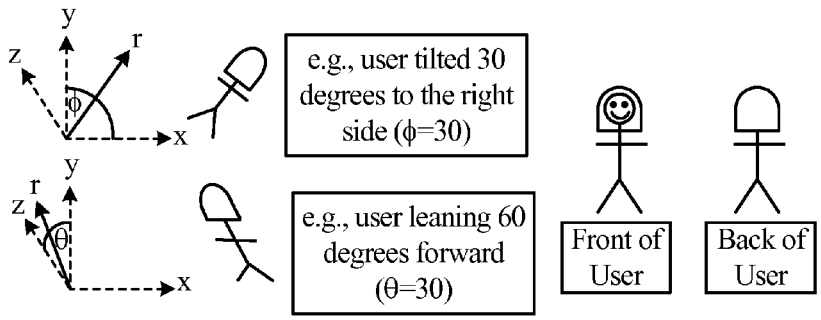
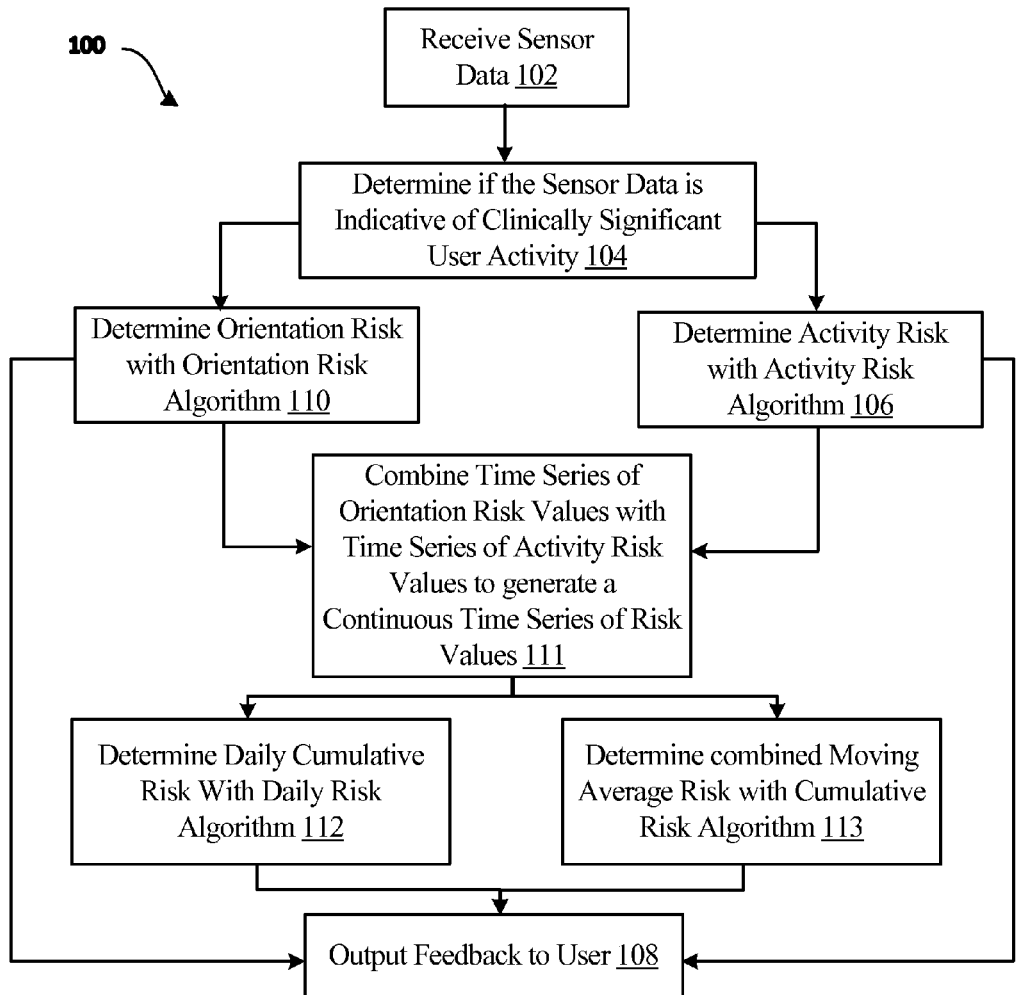

| | Theta | | | | | | | | | | | | | | | | | | | Phi |
|---|---|---|---|---|---|---|---|---|---|---|---|---|---|---|---|---|---|---|---|---|
| | | -90 | -80 | -70 | -60 | -50 | -40 | -30 | -20 | -10 | 0 | 10 | 20 | 30 | 40 | 50 | 60 | 70 | 80 | 90 |
| Headstand | 180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | 170 | 0 | 0.12 | 0.24 | 0.36 | 0.48 | 0.59 | 0.70 | 0.80 | 0.90 | 0.98 | 0.90 | 0.80 | 0.70 | 0.60 | 0.49 | 0.38 | 0.27 | 0.15 | 0.03 |
| | 160 | 0 | 0.12 | 0.23 | 0.34 | 0.45 | 0.56 | 0.66 | 0.76 | 0.85 | 0.94 | 0.86 | 0.77 | 0.67 | 0.57 | 0.47 | 0.37 | 0.26 | 0.14 | 0.03 |
| | 150 | 0 | 0.11 | 0.21 | 0.32 | 0.42 | 0.52 | 0.61 | 0.70 | 0.79 | 0.87 | 0.79 | 0.71 | 0.62 | 0.53 | 0.44 | 0.34 | 0.24 | 0.14 | 0.03 |
| | 140 | 0 | 0.09 | 0.19 | 0.28 | 0.37 | 0.46 | 0.54 | 0.62 | 0.70 | 0.77 | 0.70 | 0.63 | 0.55 | 0.47 | 0.39 | 0.30 | 0.22 | 0.12 | 0.03 |
| | 130 | 0 | 0.08 | 0.16 | 0.24 | 0.31 | 0.39 | 0.46 | 0.52 | 0.59 | 0.65 | 0.59 | 0.53 | 0.46 | 0.40 | 0.35 | 0.26 | 0.19 | 0.11 | 0.03 |
| | 120 | 0 | 0.06 | 0.12 | 0.18 | 0.24 | 0.30 | 0.36 | 0.41 | 0.46 | 0.51 | 0.46 | 0.41 | 0.36 | 0.31 | 0.26 | 0.21 | 0.15 | 0.09 | 0.03 |
| | 110 | 0 | 0.04 | 0.09 | 0.13 | 0.17 | 0.21 | 0.25 | 0.28 | 0.32 | 0.35 | 0.32 | 0.29 | 0.25 | 0.22 | 0.19 | 0.15 | 0.11 | 0.07 | 0.03 |
| | 100 | 0 | 0.02 | 0.04 | 0.07 | 0.09 | 0.11 | 0.13 | 0.15 | 0.17 | 0.18 | 0.17 | 0.15 | 0.14 | 0.12 | 0.11 | 0.09 | 0.07 | 0.05 | 0.03 |
| Flat on stomach | 90 | 0 | 0.00 | 0.00 | 0.00 | 0.00 | 0.00 | 0.01 | 0.01 | 0.01 | 0.010 | 0.01 | 0.01 | 0.01 | 0.02 | 0.02 | 0.02 | 0.03 | 0.03 | 0.03 |
| | 80 | 0 | 0.00 | 0.00 | 0.01 | 0.01 | 0.01 | 0.01 | 0.02 | 0.03 | 0.02 | 0.02 | 0.03 | 0.02 | 0.02 | 0.03 | 0.03 | 0.03 | 0.03 | 0.03 |
| | 70 | 0 | 0.01 | 0.01 | 0.02 | 0.02 | 0.03 | 0.03 | 0.04 | 0.04 | 0.03 | 0.03 | 0.03 | 0.03 | 0.04 | 0.04 | 0.04 | 0.04 | 0.03 | 0.03 |
| | 60 | 0 | 0.01 | 0.01 | 0.02 | 0.03 | 0.03 | 0.04 | 0.05 | 0.05 | 0.05 | 0.04 | 0.05 | 0.05 | 0.05 | 0.05 | 0.04 | 0.04 | 0.03 | 0.03 |
| | 50 | 0 | 0.01 | 0.02 | 0.03 | 0.03 | 0.04 | 0.05 | 0.06 | 0.06 | 0.07 | 0.06 | 0.06 | 0.06 | 0.06 | 0.06 | 0.05 | 0.04 | 0.04 | 0.03 |
| | 40 | 0 | 0.01 | 0.02 | 0.03 | 0.04 | 0.05 | 0.06 | 0.06 | 0.07 | 0.07 | 0.07 | 0.06 | 0.06 | 0.06 | 0.06 | 0.05 | 0.05 | 0.04 | 0.03 |
| Tilted forward | 30 | 0 | 0.01 | 0.02 | 0.03 | 0.03 | 0.05 | 0.06 | 0.07 | 0.08 | 0.08 | 0.07 | 0.07 | 0.07 | 0.07 | 0.06 | 0.05 | 0.05 | 0.04 | 0.03 |
| | 20 | 0 | 0.01 | 0.02 | 0.03 | 0.04 | 0.05 | 0.06 | 0.07 | 0.08 | 0.08 | 0.08 | 0.08 | 0.08 | 0.07 | 0.06 | 0.06 | 0.05 | 0.04 | 0.03 |
| | 10 | 0 | 0.01 | 0.02 | 0.03 | 0.04 | 0.05 | 0.06 | 0.07 | 0.08 | 0.09 | 0.08 | 0.08 | 0.08 | 0.07 | 0.06 | 0.06 | 0.05 | 0.04 | 0.03 |
| Standing upright | 0 | 0 | 0.01 | 0.02 | 0.04 | 0.05 | 0.06 | 0.07 | 0.08 | 0.09 | 0.100 | 0.09 | 0.08 | 0.08 | 0.07 | 0.07 | 0.06 | 0.05 | 0.04 | 0.03 |
| | -10 | 0 | 0.01 | 0.03 | 0.04 | 0.05 | 0.07 | 0.08 | 0.09 | 0.10 | 0.11 | 0.10 | 0.10 | 0.09 | 0.08 | 0.07 | 0.06 | 0.05 | 0.04 | 0.03 |
| | -20 | 0 | 0.02 | 0.04 | 0.06 | 0.07 | 0.09 | 0.11 | 0.13 | 0.14 | 0.15 | 0.14 | 0.13 | 0.12 | 0.10 | 0.09 | 0.08 | 0.06 | 0.05 | 0.03 |
| | -30 | 0 | 0.03 | 0.05 | 0.08 | 0.11 | 0.13 | 0.16 | 0.18 | 0.20 | 0.22 | 0.20 | 0.18 | 0.16 | 0.14 | 0.12 | 0.10 | 0.08 | 0.06 | 0.03 |
| Tilted backward | -40 | 0 | 0.04 | 0.08 | 0.11 | 0.15 | 0.19 | 0.22 | 0.25 | 0.28 | 0.31 | 0.28 | 0.26 | 0.23 | 0.20 | 0.17 | 0.14 | 0.10 | 0.07 | 0.03 |
| | -50 | 0 | 0.05 | 0.10 | 0.15 | 0.20 | 0.25 | 0.30 | 0.34 | 0.38 | 0.42 | 0.38 | 0.35 | 0.31 | 0.26 | 0.22 | 0.18 | 0.13 | 0.08 | 0.03 |
| | -60 | 0 | 0.07 | 0.14 | 0.20 | 0.27 | 0.33 | 0.39 | 0.45 | 0.50 | 0.55 | 0.50 | 0.45 | 0.40 | 0.34 | 0.28 | 0.22 | 0.16 | 0.11 | 0.03 |
| | -70 | 0 | 0.09 | 0.17 | 0.25 | 0.33 | 0.41 | 0.49 | 0.56 | 0.63 | 0.69 | 0.63 | 0.56 | 0.50 | 0.43 | 0.35 | 0.28 | 0.20 | 0.11 | 0.03 |
| | -80 | 0 | 0.10 | 0.21 | 0.31 | 0.41 | 0.50 | 0.60 | 0.68 | 0.77 | 0.84 | 0.77 | 0.69 | 0.60 | 0.52 | 0.43 | 0.33 | 0.23 | 0.13 | 0.03 |
| Flat on back | -90 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -100 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -110 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -120 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -130 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -140 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -150 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -160 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | -170 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| Headstand | -180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 |
| | | On left side | | | | | | | | | Middle | | | | | | | | | On right side |

Fig. 10A

| | Theta | -90 | -80 | -70 | -60 | -50 | -40 | -30 | -20 | -10 | 0 | 10 | 20 | 30 | 40 | 50 | 60 | 70 | 80 | 90 | Phi |
|---|---|---|---|---|---|---|---|---|---|---|---|---|---|---|---|---|---|---|---|---|---|
| Headstand | 180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | 170 | 0 | 0.12 | 0.24 | 0.36 | 0.48 | 0.59 | 0.70 | 0.80 | 0.90 | 0.98 | 0.90 | 0.80 | 0.70 | 0.60 | 0.49 | 0.38 | 0.27 | 0.15 | 0.03 | |
| | 160 | 0 | 0.12 | 0.23 | 0.34 | 0.45 | 0.56 | 0.66 | 0.76 | 0.85 | 0.94 | 0.86 | 0.77 | 0.67 | 0.57 | 0.47 | 0.37 | 0.26 | 0.14 | 0.03 | |
| | 150 | 0 | 0.11 | 0.21 | 0.32 | 0.42 | 0.52 | 0.61 | 0.70 | 0.79 | 0.87 | 0.79 | 0.71 | 0.62 | 0.53 | 0.44 | 0.34 | 0.24 | 0.14 | 0.03 | |
| | 140 | 0 | 0.09 | 0.19 | 0.28 | 0.37 | 0.46 | 0.54 | 0.62 | 0.70 | 0.77 | 0.70 | 0.63 | 0.55 | 0.47 | 0.39 | 0.30 | 0.22 | 0.12 | 0.03 | |
| | 130 | 0 | 0.08 | 0.16 | 0.24 | 0.31 | 0.39 | 0.46 | 0.52 | 0.59 | 0.65 | 0.59 | 0.53 | 0.46 | 0.40 | 0.35 | 0.26 | 0.19 | 0.11 | 0.03 | |
| | 120 | 0 | 0.06 | 0.12 | 0.18 | 0.24 | 0.30 | 0.36 | 0.41 | 0.46 | 0.51 | 0.46 | 0.41 | 0.36 | 0.31 | 0.26 | 0.21 | 0.15 | 0.09 | 0.03 | |
| | 110 | 0 | 0.04 | 0.09 | 0.13 | 0.17 | 0.21 | 0.25 | 0.28 | 0.32 | 0.35 | 0.32 | 0.29 | 0.25 | 0.22 | 0.19 | 0.15 | 0.11 | 0.07 | 0.03 | |
| | 100 | 0 | 0.02 | 0.04 | 0.07 | 0.09 | 0.11 | 0.13 | 0.15 | 0.17 | 0.18 | 0.17 | 0.15 | 0.14 | 0.12 | 0.11 | 0.09 | 0.07 | 0.05 | 0.03 | |
| Flat on stomach | 90 | 0 | 0.00 | 0.00 | 0.00 | 0.00 | 0.00 | 0.01 | 0.01 | 0.01 | 0.010 | 0.01 | 0.01 | 0.01 | 0.02 | 0.02 | 0.02 | 0.03 | 0.03 | 0.03 | |
| | 80 | 0 | 0.01 | 0.02 | 0.03 | 0.04 | 0.05 | 0.06 | 0.07 | 0.08 | 0.09 | 0.08 | 0.07 | 0.07 | 0.06 | 0.06 | 0.05 | 0.05 | 0.04 | 0.03 | |
| | 70 | 0 | 0.02 | 0.04 | 0.06 | 0.08 | 0.10 | 0.12 | 0.14 | 0.15 | 0.17 | 0.15 | 0.14 | 0.13 | 0.11 | 0.10 | 0.08 | 0.07 | 0.05 | 0.03 | |
| | 60 | 0 | 0.03 | 0.06 | 0.09 | 0.12 | 0.15 | 0.17 | 0.20 | 0.22 | 0.25 | 0.22 | 0.20 | 0.18 | 0.16 | 0.14 | 0.11 | 0.09 | 0.06 | 0.03 | |
| | 50 | 0 | 0.04 | 0.08 | 0.12 | 0.15 | 0.19 | 0.22 | 0.26 | 0.29 | 0.31 | 0.29 | 0.26 | 0.23 | 0.20 | 0.17 | 0.14 | 0.10 | 0.07 | 0.03 | |
| | 40 | 0 | 0.05 | 0.09 | 0.14 | 0.18 | 0.22 | 0.27 | 0.30 | 0.34 | 0.38 | 0.34 | 0.31 | 0.27 | 0.24 | 0.20 | 0.16 | 0.12 | 0.08 | 0.03 | |
| Tilted forward | 30 | 0 | 0.05 | 0.10 | 0.16 | 0.21 | 0.25 | 0.30 | 0.34 | 0.39 | 0.42 | 0.39 | 0.35 | 0.31 | 0.27 | 0.22 | 0.18 | 0.13 | 0.08 | 0.03 | |
| | 20 | 0 | 0.06 | 0.11 | 0.17 | 0.22 | 0.28 | 0.33 | 0.37 | 0.42 | 0.46 | 0.42 | 0.38 | 0.33 | 0.29 | 0.24 | 0.19 | 0.14 | 0.09 | 0.03 | |
| | 10 | 0 | 0.06 | 0.12 | 0.18 | 0.23 | 0.29 | 0.34 | 0.39 | 0.44 | 0.48 | 0.44 | 0.39 | 0.35 | 0.30 | 0.25 | 0.20 | 0.14 | 0.09 | 0.03 | |
| Standing upright | 0 | 0 | 0.06 | 0.12 | 0.18 | 0.24 | 0.30 | 0.35 | 0.41 | 0.45 | 0.500 | 0.46 | 0.41 | 0.36 | 0.31 | 0.26 | 0.21 | 0.15 | 0.09 | 0.03 | |
| | -10 | 0 | 0.06 | 0.12 | 0.19 | 0.24 | 0.30 | 0.36 | 0.41 | 0.46 | 0.51 | 0.46 | 0.42 | 0.37 | 0.32 | 0.26 | 0.21 | 0.15 | 0.09 | 0.03 | |
| | -20 | 0 | 0.07 | 0.13 | 0.19 | 0.26 | 0.32 | 0.37 | 0.43 | 0.48 | 0.53 | 0.48 | 0.43 | 0.38 | 0.33 | 0.27 | 0.22 | 0.16 | 0.09 | 0.03 | |
| | -30 | 0 | 0.07 | 0.14 | 0.21 | 0.27 | 0.34 | 0.40 | 0.46 | 0.52 | 0.57 | 0.52 | 0.46 | 0.41 | 0.35 | 0.29 | 0.23 | 0.17 | 0.10 | 0.03 | |
| Tilted backward | -40 | 0 | 0.08 | 0.15 | 0.23 | 0.30 | 0.37 | 0.44 | 0.50 | 0.56 | 0.62 | 0.56 | 0.50 | 0.44 | 0.38 | 0.32 | 0.25 | 0.18 | 0.11 | 0.03 | |
| | -50 | 0 | 0.08 | 0.17 | 0.25 | 0.33 | 0.41 | 0.48 | 0.55 | 0.62 | 0.68 | 0.62 | 0.55 | 0.49 | 0.42 | 0.35 | 0.27 | 0.19 | 0.11 | 0.03 | |
| | -60 | 0 | 0.09 | 0.18 | 0.27 | 0.36 | 0.45 | 0.53 | 0.61 | 0.68 | 0.75 | 0.68 | 0.61 | 0.54 | 0.46 | 0.38 | 0.30 | 0.21 | 0.12 | 0.03 | |
| | -70 | 0 | 0.10 | 0.20 | 0.30 | 0.40 | 0.50 | 0.59 | 0.67 | 0.75 | 0.83 | 0.75 | 0.68 | 0.59 | 0.51 | 0.42 | 0.33 | 0.23 | 0.13 | 0.03 | |
| | -80 | 0 | 0.11 | 0.22 | 0.33 | 0.44 | 0.55 | 0.65 | 0.74 | 0.83 | 0.91 | 0.83 | 0.74 | 0.65 | 0.56 | 0.46 | 0.36 | 0.25 | 0.14 | 0.03 | |
| Flat on back | -90 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -100 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -110 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -120 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -130 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -140 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -150 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -160 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | -170 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| Headstand | -180 | 0 | 0.12 | 0.25 | 0.37 | 0.48 | 0.60 | 0.71 | 0.81 | 0.91 | 1.00 | 0.91 | 0.81 | 0.71 | 0.61 | 0.50 | 0.39 | 0.27 | 0.15 | 0.03 | |
| | | On left side | | | | | | | | | Middle | | | | | | | | On right side | | |

Fig. 10B

SYSTEMS, DEVICES, AND METHODS FOR TRACKING ABDOMINAL ORIENTATION AND ACTIVITY

CROSS-REFERENCE TO RELATED APPLICATIONS

This application claims priority as a continuation of U.S. application Ser. No. 14/625,965, filed Feb. 19, 2015 and entitled "Systems, Devices, and Methods for Tracking Abdominal Orientation and Activity;" which claims priority to U.S. Provisional Application 61/971,438, filed Mar. 27, 2014 and entitled "A Method and Device to Assess and Alter Abdominal Orientation;" U.S. Provisional Application 61/986,665, filed Apr. 30, 2014 and entitled "Systems, Devices, and Methods for Tracking Abdominal Orientation and Activity;" U.S. Provisional Application 62/022,060, filed Jul. 8, 2014 and entitled "Systems, Devices, and Methods for Tracking Abdominal Orientation and Activity;" U.S. Provisional Application 62/059,557, filed Oct. 3, 2014 and entitled "Systems, Devices, and methods for Reducing Preterm Birth in Pregnant Women;" and U.S. Provisional Application 62/111,427, filed Feb. 3, 2015 and entitled "Systems, Devices, and Methods for Tracking Abdominal Orientation and Activity," all of which are hereby incorporated herein by reference in their entireties.

FIELD OF INVENTION

This invention generally uses sensing technologies and algorithms to assess and treat clinical conditions related to the abdomen.

BACKGROUND

Medical evidence suggests that large amounts of mass or pressure in the abdominal region can lead to serious health consequences. Two very closely related examples of this are intraabdominal hypertension (IAH) and abdominal compartment syndrome (ACS). In these conditions, fluid within the abdominal space accumulates in such large volumes that the abdominal wall stretches to its elastic limit. Once it can no longer expand, additional fluid leaking into the tissue results in a rapid rises in the pressure within the closed space. Initially, this increase in pressure causes mild to moderate organ dysfunction (as seen in IAH). If the pressure continues to rise to higher levels, organs may begin to fail completely (as seen in ACS), which can lead to death.

A similar pathogenesis is observed to varying degrees with morbidly obese patients and pregnant women who also can have negative clinical responses to their large abdominal masses. The abdomen as a whole may apply different amounts of pressure on intraabdominal tissues and organs depending upon its orientation to both gravity and those internal organs. As an example, consider pressure applied by the uterus of a late stage pregnant woman on her inferior vena cava (vein that runs through abdomen near the spine). The position of least pressure would be for the woman to be on her hands and knees with her abdomen hanging inferiorly. A slightly higher pressure position would be her standing upright. A higher pressure position still would be her leaning back on a couch. And the greatest amount of pressure would be experienced by her laying supine (flat on her back).

Traditionally, obstetricians have advised pregnant women with preeclampsia or other hypertensive disorders to avoid lying in the supine position and to go on bed rest for periods of time; however, these recommendations are often incomplete as they only frame the issue in terms of "good positions" (e.g. bed rest, laying on left side) and "bad positions" (e.g. laying supine).

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

In some embodiments, a wearable device for capturing abdominal orientation data and delivering feedback to the user is provided. The device may include one or more sensors which determine the spatial orientation of the user's abdomen relative to the direction of Earth's gravity and a microcontroller that receives and stores orientation data from the sensors and uses an algorithm (and/or is configured) to estimate the level of clinical risk over various time scales based on the abdominal orientation. The wearable device may further include a communication device which conveys periodic updates and alerts to the user on their current risk level.

In some embodiments, the device may be used to prevent or treat conditions of pregnancy, such as, preeclampsia, gestational hypertension, intrauterine growth restriction, fetal hypoxia, gestational diabetes, HELLP (Hemolysis, Elevated Liver Enzymes, Low Platelet count) syndrome, placenta abruption, placenta previa, or abdominal related conditions such as obesity-related hypertension, idiopathic intracranial hypertension, hypoventilation syndrome, and abdominal compartment syndrome.

Optionally, the device may also determine the position and orientation of the abdomen in relation to musculoskeletal components of the users mid-section or torso such as the spine, ribcage, back muscles, etc.

In some embodiments, the device may use geometric approximations and/or empirical reference data to determine the force, impulse, or pressure being applied to certain intra-abdominal tissues or organs by the abdomen. These tissues and organs may include the spine, kidneys, liver, bladder, all abdominal blood vessels including the inferior vena cava, and all abdominal nerves including the renal sympathetic nerves.

In further embodiments, the device may include 2 sets of sensors: one set may monitor the orientation of abdominal soft tissue (e.g. belly) and the other set may monitor orientation of an area of the torso (e.g. sternum).

In some embodiments, the wearable device may also include a fetal heart rate monitor.

In some embodiments, the device may determine acceleration forces due to movement of the user to detect walking, running, and other movements or exercise which are used in the algorithm to determine clinical risk.

Optionally, the wearable device may recommend reducing certain physical activities in order to reduce risks to the patient.

In many embodiments, the device may provide vibrational, visual, or audio feedback to the user based on past or current orientation of their abdomen. Feedback types may include: positive reinforcement for having good abdominal orientation, feedback to suggest a specific position, and feedback to suggest a different position.

In some embodiments, the microcontroller may store and later electronically transmit the orientation data and calculated intraabdominal force, impulse, or pressure data to the user or care providers, including doctors.

The device may use specialized algorithms for each patient depending on a variety of factors, including, but not limited to, user's height, weight, age, age of gestation, blood pressure, diagnostic test results, time since diagnosis, prior number of device alerts, as well as, the doctor's or patient's preference on the restrictiveness of their daily activities.

In some embodiments, the device may be used to reinforce compliance for bed rest.

Optionally, the device may contain one or more accelerometers or other sensors which can determine the orientation of the abdomen in relationship to gravity or other parts of the body.

In some embodiments the device may not send alerts to the patient, but may simply record abdominal position data to be used later.

In some embodiments, the device can be calibrated either automatically by recognizing certain characteristic position or movement data (e.g. walking, sitting, lying down), or manually by calibration by the user (e.g. press a button while standing or sitting upright).

In some embodiments, the device provides feedback only during waking hours.

Optionally, the device may be configured to send recommendations to the user or doctor to test blood pressure, urine protein, or other markers of preeclampsia.

In some embodiments, the one or more sensors comprise 1 to 3 accelerometers.

The device may be strapped to the body with elastic, Velcro, or other straps. Optionally, the device may adhere to the user with an adhesive to stick to the user's skin.

In some embodiments, the device may include a blood pressure monitor. In one embodiment, the blood pressure monitor uses pulse wave transit time to estimate absolute blood pressure or blood pressure changes. The chest strap of the device may include 2 electrodes, one on the left and one on the right side of the chest. The electrodes may transmit a current through the chest and measure impedance. This method (impedance phethysmography) is known to generate an ECG wave-form. The device may simultaneously measure the user's pulse via pulse oximetry. The device may then combine the ECG data and finger pulse rate to calculate pulse wave transit time which may be used to estimate blood pressure. In one embodiment, the pulse oximetry is performed by the camera or light sensor on a mobile phone or other mobile device that is wirelessly connected to the device.

Optionally, the device may be a mobile phone with a specialized application installed.

Alternatively, the device may be separate from a cell phone and may be configured to connect wirelessly to a cell phone with an application installed.

The device may include a sensor that sends position or activity data directly to a cell phone or mobile device which contains the algorithm and other functions detailed in this invention.

In further aspects of the present invention, a wearable device for capturing abdominal orientation data and delivering feedback to the user is provided. The device may include 1) one or more sensors, which determine the spatial orientation of the user's abdomen relative to the direction of Earth's gravity; 2) a communication device which connects the sensors to a $2^{nd}$ device which contains a microprocessor; 3) the $2^{nd}$ device that receives and stores data from the sensors and uses an algorithm to estimate the level of clinical risk over various time scales based on the abdominal orientation and/or activity level.

The $2^{nd}$ device may be a smart phone, cell phone, or other type of small computer in close proximity to or on the user, for example.

In further aspects of the present invention, a wearable device for capturing abdominal orientation data and delivering feedback to the user is provided. The device may include 1) one or more sensors, which produce data which can be translated into activities; 2) a microcontroller that receives and stores activity data from the sensors and uses an algorithm to estimate the level of clinical risk over various time scales based on type of activity and duration, and 3) a communication device which conveys periodic updates and alerts to the user on their current risk level.

The activities may include walking, running, driving, sitting, laying down, and other typical activities in which a person might participate.

In some embodiments, a method to capture abdominal orientation data and deliver feedback to the user is provided. The method may include: 1) determining the spatial orientation of the user's abdomen relative to the direction of Earth's gravity; 2) assessing whether the user's abdomen has been in an unhealthy orientation for too long of a period of time based on the determined spatial orientation of the user's abdomen, and 3) conveying alerts or suggestions to the user to indicate a need to reorient the abdomen to a different position.

In some embodiments, a wearable device system for reducing the risk of preterm birth in women may be provided. The wearable device may include one or more sensors for continuously generating sensor data indicative of an orientation of an abdomen of the user. A processor may be coupled with the one or more sensors and be configured to continuously monitor the orientation of the abdomen of the user by processing the sensor data to estimate the orientation of the abdomen of the user. The processor may further identify orientation risk values associated with the estimated orientations of the abdomen to produce a time series of identified orientation risk values. A first cumulative risk value may be calculated and updated by calculating a first moving average for a subset of the time series of identified orientation risk values associated with the estimated orientations of the abdomen. The subset for the first moving average may have a first size. The first size may be at least the last 30 seconds of sensor data. In some embodiments, it may be the last two minutes of sensor data. Thereafter the processor may compare the first cumulative risk value to a first threshold and output a warning when the first cumulative risk value crosses the first threshold.

Optionally, the sensor data comprises a recline angle and a sideways tilt angle. The orientation risk values may be a function of the recline angle and the sideways tilt angle.

In some embodiments, the processor may be further configured to receive blood pressure data of the user. The processor may raise or lower the first threshold in response to the received blood pressure data.

The system may further include a blood-oxygen level sensor for generating blood-oxygen level data of the user. The blood oxygen level sensor may be coupled with the processor. The processor may raise or lower the first threshold in response to the blood-oxygen level data from the blood oxygen level sensor.

An input may be coupled with the processor. The input may be configured to receive a user input of pregnancy factors comprising at least one of a multiple pregnancy of the user, body mass index (BMI) of the user, prior live births of the user, and preexisting hypertension of the user. The processor may raise or lower the first threshold in response to the user input of pregnancy factors.

The processor may be further configured to calculate and update a second cumulative risk value by calculating a second moving average for a subset of the time series of identified orientation risk values. The subset for the second moving average may include at least the last 5 seconds of sensor data. The processor may compare the second cumulative risk value to a second threshold and output a warning when the second cumulative risk value crosses the second threshold.

The processor may be further configured to continuously monitor user activity by processing the sensor data to calculate user experienced force changes to identify clinically significant user activity. The force changes may be calculated by identifying a difference between a max force and a minimum force in the sensor data during a time interval. A time series of calculated force changes may be generated by the processor.

In some embodiments, the processor may identify clinically significant user activity by calculating and updating a user activity moving average for a subset of the time series of calculated force changes associated with the user activity. Thereafter the processor may compare the user activity moving average to an activity threshold to determine whether the user is engaged in clinically significant activity. Optionally, the processor may record a cumulative time duration of the clinically significant activity engaged by the user over a period of time.

In some embodiments, an input may be provided and coupled with the processor. The input may be configured to receive user input of a gestational age of a pregnancy of the user.

The processor may be further configured to compare the cumulative time duration of clinically significant activity engaged by the user over the period of time to a preferred cumulative activity threshold specific for the gestational age of the pregnancy of the user.

In some embodiments, when the processor identifies clinically significant user activity, the processor may stop identifying orientation risk values. The processor may be further configured to identify activity risk values associated with the force changes to produce a time series of identified activity risk values. The processor may calculate and update the first cumulative risk score by combining the time series of identified activity risk values and previously identified orientation risk values and calculating a moving average for a subset of the combined time series of identified activity risk values and previously identified orientation risk values.

In some embodiments the system may include an infrared sensor coupled with the processor. The processor may determine device use in response to infrared sensor data.

Optionally, processor may be further configured to compare the first cumulative risk value to a second threshold and output a warning when the first cumulative risk value crosses the second threshold. The warning associated with the first threshold and the warning associated with the second threshold may be different.

In yet another aspect of the present invention, a system may be provided that includes a processing device and a non-transitory computer-readable medium accessible by the processing device. The processing device may be configured to execute logic embodied in the non-transitory computer-readable medium and thereby perform operations including: (1) receiving force measurements from a sensor; (2) calculating force changes over time using the received force measurements; (3) determining whether the user is engaged in clinically significant activity based on the calculated force changes and an activity threshold.

When the user is determined to not be engaged in clinically significant activity, the processor may carry out the steps of: (a) receiving a recline angle and a sideways tilt angle from a sensor; (b) identifying orientation risk values associated the received recline angle and the received sideways tilt angle; and (c) recording a time series of orientation risk values;

When the user is determined to be engaged in clinically significant activity, the processor may carry out the steps of: (a) identifying activity risk values associated with the force changes and (b) recording a time series of activity risk values.

The processor may further be configured to combine the recorded time series of orientation risk values with the recorded time series of activity risk values to generate a continuous time series of risk values. A cumulative risk may be calculated on a subset of the continuous time series of risk values by calculating a moving average for a subset of the continuous time series of risk values. Thereafter, the processor may be configured to carry out the steps of: comparing the cumulative risk to a cumulative risk threshold value and outputting a warning when the cumulative risk crosses the cumulative risk threshold value.

Optionally, the processing device, by executing the logic, may be further configured to perform additional operations comprising: when the user is determined to be engaged in activity, recording a cumulative time duration of the clinically significant activity by the user over a period of time and comparing the cumulative time duration of the clinically significant activity engaged by the user over the time period to a preferred cumulative activity threshold.

The preferred cumulative activity threshold may be dependent on a pregnancy stage of the user.

The system may further include the sensor. The may be housed in a first housing and the processor may be housed in a second housing separate from the first housing. The sensor may be wirelessly coupled with the processor.

In further embodiments, a method for reducing the risk of preterm birth in women is provided. The method may include receiving sensor data from a sensor coupled with a user and determining whether the user is engaged activity based on the received sensor data. When the user is determined to not be engaged in activity, the method may include monitoring the orientation of the abdomen of the user by processing the sensor data to estimate the orientation of the abdomen of the user and identifying orientation risk values associated with the estimated orientations of the abdomen to produce a time series of identified orientation risk values. Thereafter, the method may include calculating and updating a cumulative risk value by calculating a first moving average for a subset of the time series of identified orientation risk values associated with the estimated orientations of the abdomen and comparing the cumulative risk value to a first threshold and a second threshold. A first warning may be outputted when the cumulative risk value crosses the first threshold and a second warning when the cumulative risk value crosses the second threshold.

The method may further include, when the user is determined to be engaged in clinically significant activity, stopping the producing of the time series of identified orientation risk values and identifying activity risk values associated with the sensor data to produce a time series of identified activity risk values. Calculating and updating the cumulative risk score may be performed by combining the time series of identified activity risk values and previously identified orientation risk values and calculating a moving average for a subset of the combined time series of identified activity risk values and previously identified orientation risk values.

In further embodiments, a wearable device system for reducing the risk of preterm birth in women is provided where the wearable device may include one or more sensors for continuously generating force data indicative of an activity of the user. A processor may be coupled with the one or more sensors and be configured to continuously monitor the activity of the user by processing the force data to identify force changes in the force data to estimate a vigorousness of the activity of the user. The processor may compare the identified force changes to a force change threshold value to determine whether the user is engaged in clinically significant activity. When the user is engaged in clinically significant activity, the processor may be configured to identify activity risk values associated with the identified force changes to produce a time series of identified activity risk values. The processor may also calculate and update a cumulative risk value by calculating a moving average for a subset of the time series of identified activity risk values associated with the identified force changes and compare the cumulative risk value to a threshold. A warning may be outputted when the first cumulative risk value crosses the first threshold.

The force changes may be calculated by identifying a difference between a max force and a minimum force in the force data during a time interval and the processor may produce a time series of calculated force changes. Optionally, the processor identifies clinically significant user activity by: calculating and updating a user activity moving average for a subset of the time series of calculated force changes associated with the user activity and comparing the user activity moving average to an activity threshold to determine whether the user is engaged in clinically significant activity. The processor may further record a cumulative time duration of the clinically significant activity engaged by the user over a period of time.

An input may be provided that is coupled with the processor and configured to receive user input of a gestational age of a pregnancy of the user. The processor may be further configured to compare the cumulative time duration of clinically significant activity engaged by the user over the period of time to a preferred cumulative activity threshold specific for the gestational age of the pregnancy of the user.

In one embodiment, the device is used to train the user which orientations and activities are preferable so that the device does not need to be worn through the entire course of pregnancy. The device may be used initially for a few hours or days or may be used periodically throughout pregnancy to refresh the user's memory as to which activities and orientations are preferred. The reminders can come in the form of alerts, text messages, alarms, or any other known form of reminder to the user. In a further embodiment, the training device comprises an app on a mobile device which is attached to the user's torso.

In further embodiments, a device may be provided for inhibiting preeclampsia of a woman. The device may include a sensor configured to generating orientation data and a support configured to couple the sensor to an abdomen of the woman such that the orientation data is indicative of an orientation of the abdomen. A processor may be coupled to the sensor so that it receives the orientation data. The processor may be configured to calculate a time series of values in response to the data and a cumulative risk value in response to the calculated values. The processor may have an output for transmitting a warning in response to the risk value such that preeclampsia risk is mitigated.

While multiple embodiments are disclosed, still other embodiments will become apparent to those skilled in the art from the following detailed description, which shows and describes various illustrative embodiments. As will be realized, the various implementations are capable of modifications in various obvious aspects, all without departing from the spirit and scope of those embodiments. Accordingly, the drawings and detailed description are to be regarded as illustrative in nature and not restrictive.

BRIEF DESCRIPTION OF THE DRAWINGS

FIG. 7 illustrates an exemplary coordinate system for the user and the device;

FIG. 8 illustrates an exemplary operational flow according to some embodiments;

FIGS. 10A-10B illustrate exemplary orientation risk value matrices;

DETAILED DESCRIPTION

Figure 1:
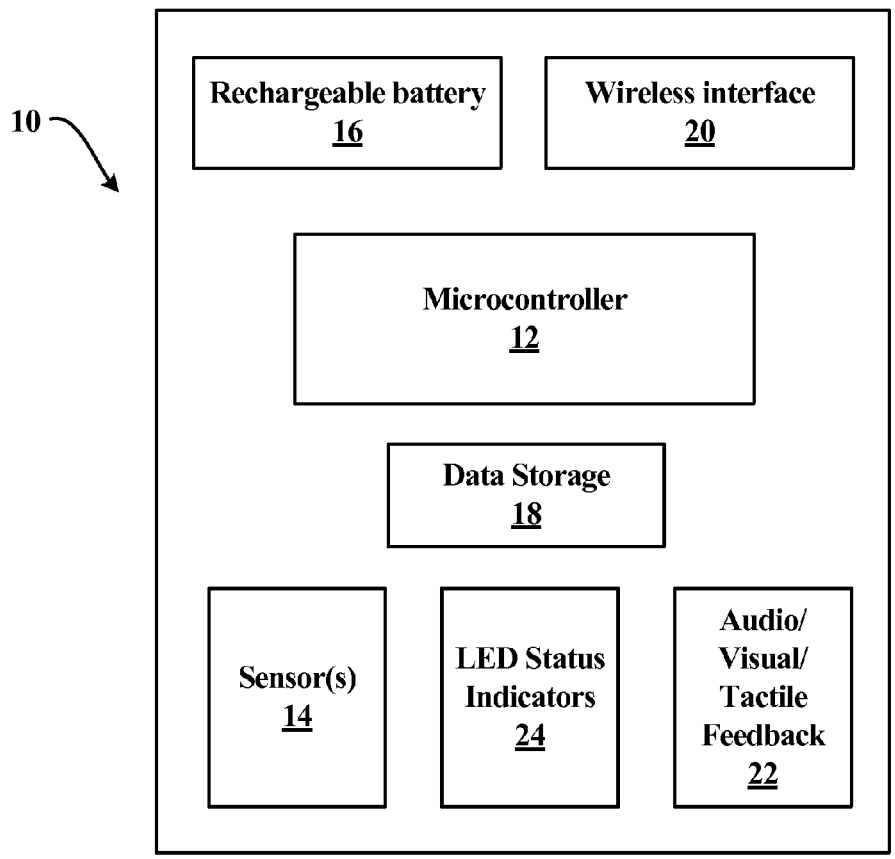
FIG. 1 illustrates a system diagram of an exemplary device for tracking abdominal orientation and/or user activity.

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Many embodiments of the invention provide systems, devices, and methods to track abdominal orientation and provide clinically relevant feedback to the patient and/or physician in order to prevent, avoid, or reverse diseases or conditions that are related to abdominal position.

Some embodiments provide for a wearable device for capturing abdominal orientation data and delivering feedback to the user. The device may include 1) one or more sensors which determine the spatial orientation of the user's abdomen (e.g., relative to the direction of Earth's gravity); 2) a microcontroller that receives and stores orientation data from the sensors and estimates the level of clinical risk over various time scales based on the abdominal orientation, and 3) a communication device and/or output which conveys periodic updates and alerts to the user on their current risk level.

Embodiments of the present invention may calculate the risk associated with a plurality of abdomen positions and perform a calculation based on the accumulated risk of each of the plurality of positions over a period of time. There may be high risk and low risk positions but since it is an accumulated calculation, there may be no positions that are off limits. Some positions may be tolerated longer than others. For example, a pregnant woman's IVC may be temporarily occluded if she lies in the supine position. If she only spends a few seconds in that position and then rolls over on her side, blood flow will resume and she will be fine; however, if she continues to move back to the supine position repeatedly, blood flow may be restricted to a variety of abdominal organs and she could be at risk for either an acute organ dysfunction, or a prolonged stress that leads to a chronic organ dysfunction or failure. Accordingly, some embodiments of the present invention estimate the pressure, mechanical force, and/or impulse placed on intraabdominal organs over short time periods (e.g., seconds, minutes, or the like) and/or over very long time periods (e.g., months) and may alert or notify patients and/or clinicians if patients are experiencing too much cumulative pressure on their organs and tissues.

Advantageously, some embodiments of the systems, devices, and methods may be customized for different patients. For example, different women with different physical attributes or severities of disease may benefit from systems, devices, and methods utilizing specialized programs. In some embodiments, the risk assessment and type of feedback provided by the device may be influenced by a number of factors. For example, some factors that may be accounted for include the user's height, weight, age, age of gestation, blood pressure, diagnostic test results (genetic tests, blood tests, urine tests, etc.), time since diagnosis, prior number of device alerts, and/or the doctor's or patient's preference on the restrictiveness of their daily activities. Accordingly, in some embodiments, one or more of these factors may be inputted to create a customized algorithm for individual patients. As an example, one patient might have preexisting hypertension, be obese, be at 35 weeks of gestation, and have a positive diagnostic result for genetic predisposition to preeclampsia. Once these factors are input into the algorithm, the systems, devices, or methods may calculate that the patient is at higher risk for preeclampsia and may then provide alerts to the patient that are appropriate for higher risk patients. For example, a customized device or system may be more sensitive for higher risk patients—alerting the patient even when the patient has not spent a lot of time in positions that are highly contributive to pressure on intraabdominal organs. In another example, some embodiments may determine that a young, healthy woman at 20 weeks of gestation is at a lower risk for preeclampsia and may then provide alerts to the patient that are appropriate for lower risk patients. Accordingly, the patient may receive no warnings even when the patient has spent a similar amount of time in similar positions as the higher risk patient.

In some embodiments, daily reports may be generated and outputted to the patient and/or clinician. For example, the reports may notify a patient that she was not at high risk and does not need to alter her daily activities or abdominal position from her current normal daily routine.

In some embodiments, clinical recommendations may be provided to a patient or clinician. For example, some systems and devices may be configured to suggest that the patient check their blood pressure, take a proteinurea test, or check in with their doctor.

As preeclampsia may take months to develop, some embodiments may be configured to provide feedback during extended periods of time to ensure the intraabdominal region is not subject to preeclampsia-inducing levels of pressure over time, thus preventing the syndrome from beginning, preventing it from progressing further, and/or reversing it.

Some embodiments prevent fetal hypoxia by limiting the amount of time that blood flow is restricted to the placenta and fetus. Since fetal hypoxia results in children with decreased IQ and increased likelihood of learning disabilities, some embodiments could improve cognitive abilities of children.

While the above examples are generally discussed with reference to avoiding preeclampsia and other complications of pregnancy, it should be understood that embodiments disclosed herein may be applicable to preventing other conditions as pressure on abdominal veins and organs can be harmful outside of pregnancy as well. In some circumstances, people with idiopathic intracranial hypertension (IIH) who have severe intractable headaches which often do not respond to standard pharmacotherapy may benefit from embodiments disclosed herein. IIH occurs almost exclusively in obese patients which large amounts of abdominal fat. Research has shown that lifting this fat tissue away from the center of the body may relieve adverse symptoms in some patients. Accordingly, some embodiments of the invention may provide positional feedback to prevent the severe headaches from forming.

In some embodiments, a sensing device may measure patient position and may send that data in real time or periodically (e.g., every few hours) to the patient's phone or other Wi-Fi/Bluetooth device.

In some embodiments, algorithms may use physics and clinical approximation to determine how much pressure has been placed on a patient's IVC. In further embodiments, the algorithm may use geometric approximations of the belly size, shape, and constitution in order to predict how much force due to gravity (or movement) is applied to various areas of the intraabdominal space.

Some embodiments may involve taking actual patients in different positions and using imaging techniques and empirical observation to determine how much pressure is applied to the intraabdominal space for different positions. This empirical data may then be used to construct an algorithm. This algorithm may be continually updated over time as more empirical data is gathered.

In some embodiments, position and activity data may be transmitted to a doctor or other care provider so the doctor knows how compliant the patient has been with instructions for bed rest or reduced activity.

In some embodiments, the device may be placed on the shoulder, neck, chest, abdomen, hip, or other area near the abdomen that moves in a similar manner to the abdomen.

In further embodiments, the device may be placed on the arm, wrist, leg or other area remote from the abdomen, and a more complex algorithm may be used to approximate abdominal position and activity.

In further embodiments, the device may be placed in the vagina.

In further embodiments, one or more sensors may be placed on or near the abdomen to detect abdominal position, and one or more sensor may be placed on an extremity to detect activity type and level.

In some embodiments, the device may be attached to patient clothing.

In some embodiments, the device has a very low profile so it cannot be easily seen through clothes if it is on the body.

In some embodiments, the user stands straight up or sits upright and presses a button to calibrate the device.

In some embodiments, the device may have a heat sensor. If the heat sensor detects the device is not on the body, it may require the patient to recalibrate the device once in contact with the body again. This may prevent a patient from "gaming" the system and also may prevent incorrect position or activity data to result from failure to recalibrate if the device is temporarily removed or adjusted.

In some embodiments, the device may be used prophylactically to prevent various medical conditions from developing. These conditions include preeclampsia, hypertensive pregnancy, idiopathic intracranial hypertension and a host of other diseases and conditions referenced in this invention.

In some embodiments, the device requires recalibration if a minimal level of movement or vibration is not detected over asset period of time.

In some embodiments, the doctor or care provider can communicate directly to the patient via the device. This may include recommendations to lower activity or change positions based on data the doctor receives from the device, or may include communication unrelated to the data generated by the device.

In some embodiments, the algorithm may leverage the network effect of gathering lots of data from different users to hone the algorithm.

In some embodiments, the algorithm may be sensitive to total accumulated load vs. length of time per incident. For example, in some embodiments, the algorithm may be based on an understanding that it is clinically preferable to apply pressure to abdominal veins 100 times for 1 min each as compared to 1 time for 100 min.

In some embodiments, the device provides specific advice, such as, "go on hands and knees for 2 min" or "don't lean back so far" vs. a generic uniform "poor position" alert.

In some embodiments, different parts of the abdomen may be used for orientation calculations including belly button or estimated center of gravity In some embodiments, the device estimates of the center of gravity of the soft tissue in relationship to the musculoskeletal system. In some embodiments this may be done with 2 sensors (one on soft tissue (e.g., belly button) and one on skeleton (e.g., sternum)). In further embodiments, just one sensor may be used which requires empirical or theoretical data to determine where abdominal soft tissue would be expected to be in relationship to interior vessels or other tissues/organs, depending on the age of gestation, height and weight, and number of fetuses etc.

In some embodiments, a number of impulse vectors on different organs and tissues may be estimated by the device.

In some embodiments, the global intraabdominal pressure or regional intraabdominal pressures are estimated by the algorithm.

In some embodiments, the device captures various activities like running, driving, etc. and assigns specific values to those which are different for near term and long term analysis. For example, in some embodiments, the device alerts a woman to take a break after 10 minutes of jogging or 30 min of walking, but the algorithm views those short duration as net positives over the period of days or weeks.

In some embodiments, the algorithm views an activity as beneficial for abdominal health initially but later views it as detrimental to health after a certain threshold time. For example, in some embodiments, walking may be initially viewed as beneficial, but reaches an inflection point at 30 minutes, at which point, it may be viewed as detrimental.

In some embodiments, the device alerts the user as to when they should take daily aspirin to prevent preeclampsia.

In some embodiments, the mechanism of action that induces preeclampsia may be the compression of abdominal sympathetic nerves or arterial system, rather than, or in addition to, the venous system.

In some embodiments, the device may be diagnostic as well as therapeutic. The device may use data mining to determine which activity profiles more often lead to preeclampsia. The device may then warn patients to be extra vigilant who have similar activity/orientation profiles.

In some embodiments, the daily % compliance with bed rest and/or reduced activity may be sent to the patient and/or doctor.

In some embodiments, the application or software for the device may comprise a comprehensive diagnostic and therapy system that suggests a variety of tests and treatments for pregnant women. In some embodiments, based on a patient's risk profile, the app suggests the patient get a diagnostic test (blood protein markers or genetic based) to see if they are at high risk for any pregnancy diseases. Manual patient data inputs, diagnostic test results, as well as position and activity monitor data may all feed into one comprehensive algorithm that continually assesses a patient's estimated risk for disease initiation and progression and offers feedback to help manage risk.

FIG. 1 illustrates an exemplary device 10 according to some embodiments of the present invention. The device 10 may include a microcontroller (processor) 12 coupled with one or more sensors 14. The device 10 may be powered by a rechargeable battery 16. Data storage 18 may be provided to store computer software executable by the microcontroller 12 and the received sensor data from the one or more sensors 14. The device 10 may further include a wireless interface 20 for interfacing with other devices (e.g., smart phone, computer, etc.). Device 10 may further include an audio/visual/tactile feedback device 22 for outputting signals to a device user. LED status indicators 24 may also be provided.

Device 10 may be a wearable device for capturing abdominal orientation data and delivering feedback to the user. The device 10 may provide precision tracking of both fast and slow motions of the user. In some embodiments, the device 10 may provide altitude tracking, pressure readings, temperature readings, and/or user pedometer readings.

The microcontroller 12 may be configured to receive and process the sensor data from the one or more sensors 14. In many embodiments, the microcontroller 12 may be configured to monitor user activity to identify risks associated with certain levels of activity to the user. In many embodiments, the microcontroller 12 may be configured to monitor user orientation to identify risks associated with certain user orientations. Optionally, the microcontroller 12 may be configured to transmit the sensor data from the one or more sensors 14 to a processor housed separately from the device 10 for data analysis at the separate processor. This may be beneficial when increased processing power is desired and/or when reducing a footprint of device 10. The separate processor may be a portable electronics device (e.g., PDA, smartphone, tablet computer, watch, or the like) of the user, a desktop computer (a personal computer of the user, a clinician's computer), etc.

The one or more sensors 14 may include accelerometers, gyroscopes, magnetometers, infrared/temperature sensors, pressure sensors, and/or combinations thereof. In some embodiments, the one or more sensors 14 may be 3-axis sensors (e.g., 3-axis gyroscopes, 3-axis accelerometers, 3-axis magnetometers, etc.). Optionally, the one or more sensors 14 may comprise a plurality of single axis sensors (e.g., one or more of: x-axis gyroscopes, y-axis gyroscopes, z-axis gyroscopes, x-axis accelerometer, y-axis accelerometer, z-axis accelerometer, x-axis magnetometers, y-axis magnetometers, z-axis magnetometers, etc.).

For example, in some embodiments, device 10 may feature a user-programmable gyroscope full-scale range of ±250, ±500, ±1000, and ±2000°/sec (dps). In some embodiments, device 10 may feature a user-programmable accelerometer full-scale range of ±2 g, ±4 g, ±8 g, and ±16 g. In some embodiments, device 10 may feature a magnetometer full-scale range of ±4800 µT. Device 10 may further include analog-to-digital converters for digitizing the output from the one or more sensors 14 for data recording and analysis.

In some embodiments, the one or more sensors 14 may include an infrared sensor. The infrared sensor may be configured to provide data that is indicative of when the device 10 is being worn by the user. Optionally, the processor 12 may signal a device alert to signal insufficient coupling of the device 10 to the user based on received infrared data from an infrared sensor. In some embodiments, the processor 12 may trigger a device sleep mode, power saving mode, or off mode when the infrared sensor data indicates that the device 10 is decoupled from the user.

In many embodiments, the one or more sensors 14 may provide force data (e.g., $F_x$, $F_y$, $F_z$) and/or orientation data (e.g., a recline angle $\theta$, a side tilt angle $\phi$) to the microcontroller 12 for processing. Exemplary processing algorithms are discussed further below.

The rechargeable battery 16 may be an Li-ion battery for example. The battery 16 may be recharged via a Universal Serial Bus (USB) port, mini-USB port, micro-USB port or the like.

Wireless interface 20 may provide wireless connection to smartphones, tablets, or other mobile devices. For example, in some embodiments, data may be stored on the device 10 and transmitted for processing at a later time. Alternatively, the device 10 may transmit the data in substantial real-time to a user's personal electronics device for data processing. In some embodiments, the wireless interface 20 may be a Wi-Fi or Bluetooth wireless interface.

The feedback device 22 may be one or more displays, light indicators, speaker(s), and/or vibration motor(s) for outputting signals to a device user. For example, a display may display risk scores, orientations, activity levels, etc. to a user.

Additionally or alternatively, light indicators may provide a meter output. For example, light indicators may be a row of five lights that progressively light up to provide a warning to a user. Optionally, the light indicators may provide various color outputs for different degrees of warning (e.g., green, yellow, red, etc.).

The feedback device 22 may also provide an audio output. For example, the feedback device 22 may provide beeping warnings or vocal feedback/suggestions to the user. The feedback device 22 may also provide a haptic feedback with a vibration motor.

LED status indicators 24 may signal power status, battery status, Wi-Fi status, Bluetooth connectivity status or the like.

Figure 2:
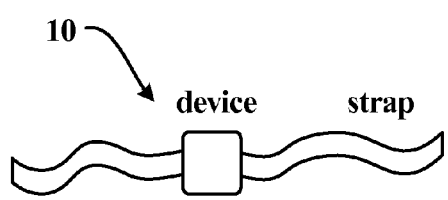
FIG. 2 illustrates an exemplary wearable device for tracking abdominal orientation and/or user activity which attaches to a user by straps.

FIG. 2 illustrates an exemplary wearable device 10 for tracking abdominal orientation and/or activity which attaches to a user by straps 26. The device 10 may be strapped to the body with elastic, Velcro, or other straps. The straps 26 may be adjustable and may couple to the device 10 and/or to each other via buckles, clasps, fasteners, buttons, or the like.

Figure 3:
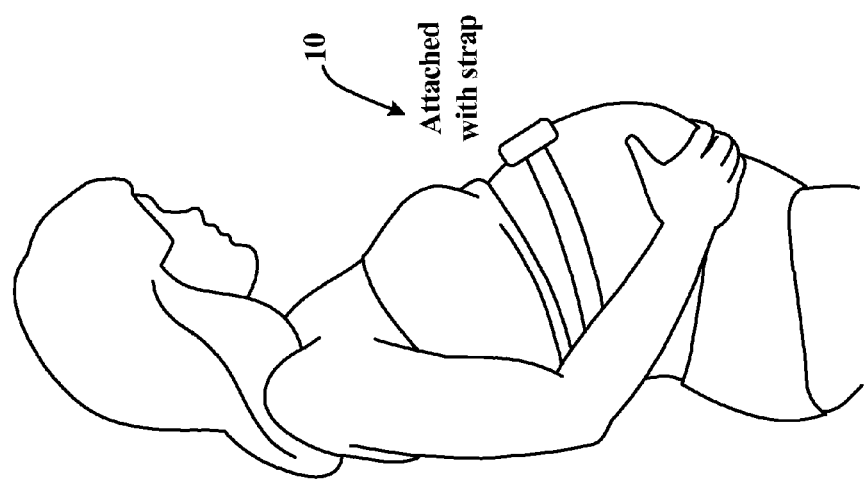
FIG. 3 illustrates the exemplary wearable device of FIG. 2 placed on and attached to a user at an exemplary location.

FIG. 3 illustrates the exemplary wearable device of FIG. 2 placed on and attached to a user at an exemplary location. In many embodiments, the device 10 may be strapped to a position above the user's belly button. While this position may be preferred for some implementations, it should be understood that other mounting positions are possible.

Figure 4:
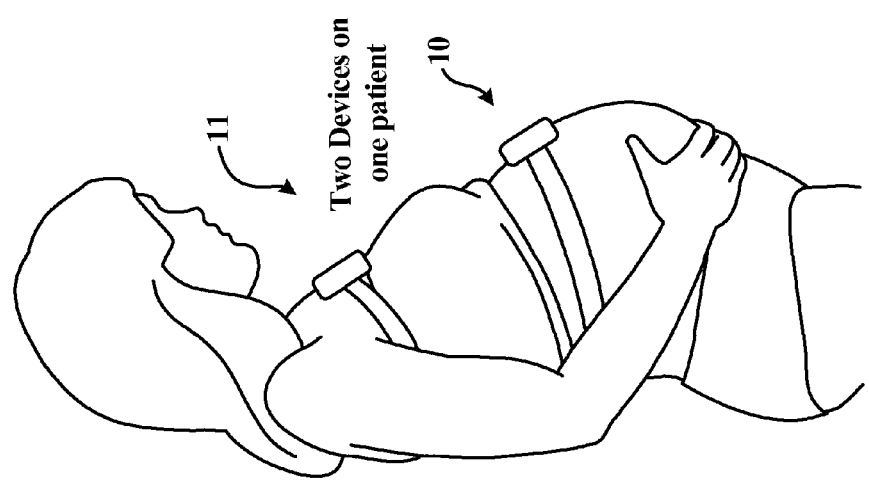
FIG. 4 illustrates an exemplary system for tracking abdominal orientation and activity including the exemplary wearable device of FIG. 2 in combination with another exemplary wearable device for tracking abdominal orientation and activity (which may be identical to the exemplary wearable device illustrated in FIG. 2)

FIG. 4 illustrates an exemplary system for tracking abdominal orientation and/or user activity including the exemplary wearable device of FIG. 2 in combination with another exemplary wearable device for tracking abdominal orientation and/or user activity (which may be identical to the exemplary wearable device illustrated in FIG. 2). Device 11 may be strapped or otherwise attached near the user's sternum. In the illustrated system, the two wearable devices 10, 11 may cooperate to provide additional sensor data. The additional sensor data from device 11 may provide more accurate results when monitoring user orientation and/or user activity.

Figure 5:
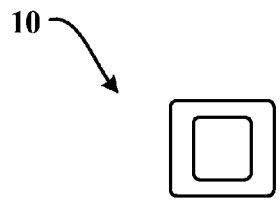
FIG. 5 illustrates an exemplary wearable device for tracking abdominal orientation and activity which attaches to a user by an adhesive back.

Optionally, the device 10 may adhere to the user with an adhesive to stick to the user's skin. FIG. 5 illustrates an exemplary wearable device 10 for tracking abdominal orientation and activity which attaches to a user by an adhesive back 28. The adhesive back 28 may be a medical grade skin adhesive.

Figure 6:
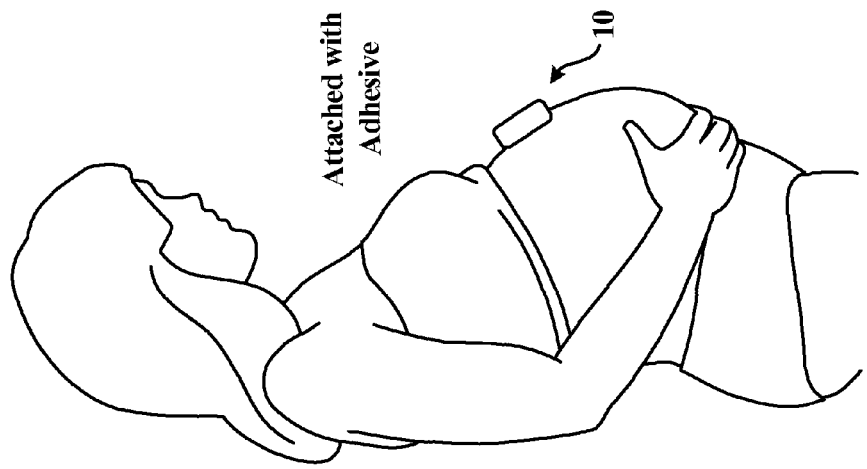
FIG. 6 illustrates the exemplary wearable device of FIG. 5 placed on and attached to a user at an exemplary location.

FIG. 6 illustrates the exemplary wearable device 10 of FIG. 5 placed on and attached to a user at an exemplary location. The device 10 may be adhered to a position centered above the user's belly button. Optionally, it may be positioned between the user's belly button and the user's sternum. It may be preferable in some embodiments for the sensor to be flat against the body along the symmetry line of the body. Accordingly, the sensor device may be placed on the belly button, on top of the belly, or anywhere along the sternum. In other embodiments, the device may be placed on a non-centerline position but may require a two-step calibration where the body is in two distinct orientations so that the device would know which direction is "forward" and which was "backward".

In some embodiments, the device 10 may be attached to human skin using Velcro where one Velcro strip is attached to the device 10 and the other Velcro strip had adhesive for attachment to the skin (e.g., medical grade skin adhesive). In such a configuration, the device 10 may be easily removed and reattached to the body. The Velcro strip on the skin may remain on for longer durations of time (hours to days) depending upon the preference of the patient.

Optionally, the components of device 10 may be distributed so they are in the same plane and spread out over a larger surface area. This may allow the device to have a lower profile or even integrated into a user's clothing or attached thereto. This may help secure the device 10 to a fixed orientation so that the device 10 may not need recalibration due to unintended reorientation of the device 10 on the body.

In some embodiments, the housing of device 10 may be flexible so as to conform to the curvature of the user's body. Optionally, the housing of device 10 may be rigid but may include a curved inner surface (i.e., the surface closest to the user) that generally approximates the curvature of the user's belly.

As discussed above, the sensor data may include force data and orientation data. The force data may be $F_x$, $F_y$, $F_z$ force data. The orientation data may be a recline (pitch) angle ($\theta$) and a side tilt (roll) angle ($\phi$).

Orientation in 3 dimensions may be defined as follows:
x=g's of force from x-sensor (axis of person's left hip to right hip)
y=g's of force from y-sensor (axis of feet to head)
z=g's of force from z-sensor (axis of back to front)
The recline angle (theta) and sideways tilt angle (phi) may be calculated with the following equations:

$r=\text{sqrt}(x^2+y^2+z^2)$ $\text{phi}(\phi)=\arctan(x/y)*180°/\pi$ $\text{theta}(\theta)=\arctan(z/y)*180°/\pi$ FIG. 7 illustrates an exemplary coordinate system for the user and the device. Forces along the user's left to right side may be represented by measured forces along the x-axis (left side to right side of the device). Forces along the user's vertical axis (e.g., feet to head) may be represented by measured forces along the y-axis (bottom of the device to the top of the device). Forces from the user's back to front may be represented by measured forces along the z-axis (front surface to back surface of the device).

Also illustrated, rotation values around the x-axis (called the recline angle and represented by θ) may range from lying face down to sitting/standing straight up to lying face up. Further, rotation values around the z-axis (called the side tilt angle and represented by φ) may range from lying on the left side to sitting/standing straight up, to lying on the right side. It should be understood that the illustrated coordinate system is exemplary and not limiting.

In some embodiments, the device may be calibrated by standing and calibrating the device so that forces in the x-axis and z-axis are equal to 0 and forces along the y-axis equals 1. Optionally, the calibration procedure may provide a brief pause (e.g., 1-5 seconds) between when the user presses a calibration start button and when the calibration calculations begin in order to allow the user to get into a preferred position.

The calibration may be performed by taking the average of each of the x, y, and z values over a time or measurement period (e.g., last 10 measurements or last 1-10 seconds) and checking to see if values of each of the x, y, and z variables are relatively unchanged. If unchanged, the calibration constants may be recorded. For example, if measurements are received at 0.1 second increments, at 0.1 seconds, a first data point may be recorded ($x_1$, $y_1$, $z_1$), at 0.2 seconds, a second data point may be recorded ($x_2$, $y_2$, $z_2$) and so on over the calibration time period (1-10 seconds for example). The new data point generated every 0.1 seconds may be put into a new variable (e.g., $x_{new}$, $y_{new}$, $z_{new}$). At every 0.1 second increment, the calibration algorithm may check if the subsequently received values are within a desired percentage (1-5%) of the initial reading (e.g., $x_1$, $y_1$, $z_1$). For example, the algorithm may check to see if the new variables are within 2% of the initial reading:

$0.98*x_{new} \leq x_1 \leq 1.02*x_{new}$ $0.98*y_{new} \leq y_1 \leq 1.02*y_{new}$ $0.98*z_{new} \leq z_1 \leq 1.02*z_{new}$ If the equation is satisfied, it may continue to the next measurement. If at any point, any of the values are not within the desired percentage, the calibration sequence may restart with a new initial reading (e.g., $x_1$, $y_1$, $z_1$). When the calibration time period (1-10 seconds for example) passes without any of the x, y, or z values fluctuating more than the desired percentage (e.g., 2%), the calibration constants may be recorded and an orientation calibration may be performed where:

$$cal.theta = \arctan\left(\frac{z_1}{y_1}\right)$$

$$cal.phi = \arctan\left(\frac{x_1}{y_1}\right)$$

Variables cal.theta and cal.phi may be subtracted from the raw theta and raw phi values.

In some embodiments, the following alternate xyz plane is defined as:
y=g's of force from y-sensor (axis of person's left hip to right hip)
x=g's of force from x-sensor (axis of feet to head)
z=g's of force from z-sensor (axis of back to front)
In some embodiments, the phi and theta equations are modified in order to stabilize the functions where:

$r=\text{sqrt}(x^2+y^2+z^2)$ $\text{phi}(\phi)=\arctan(y/\text{sqrt}(x^2+z^2))*180°/\pi$ $\text{theta}(\theta)=\arctan(-x*(\text{sign of } z)/\text{sqrt}(z^2+u*y^2))*180°/\pi$ where u is a constant with a preferred range between 0.001 and 0.3, and where "sign of z" simply inserts a negative 1 when z is negative and a positive 1 when z is positive.

FIG. 8 illustrates an exemplary operational flow 100 according to some embodiments of the device 10. Sensor data may be received 102. From the sensor data, a processor may determine if the sensor data is indicative of significant user activity 104. If the sensor data is indicative of significant user activity, the processor may further analyze the sensor data to monitor user activity and determine activity risk with an activity risk algorithm 106. Based on the monitoring 106, the processor may output feedback to a user 108. When the sensor data is indicative of a user not engaged in significant activity, the processor may analyze the sensor data to monitor user orientation and determine orientation risk with an orientation risk algorithm 110. Based on the monitoring 110, the processor may output feedback to a user 108. Additionally, in some embodiments, the processor may be configured combine a time series of orientation risk values obtained from algorithm 110 and a time series of activity risk values obtained from algorithm 106 to generate a continuous time series of risk values 111. The continuous time series of risk values may then be used to determine a daily cumulative risk 112 over an extended time period (e.g., 24 hours starting and ending each day at 3 a.m.). The daily cumulative risk may be a function of the risk values obtained from the monitoring 106 and/or the monitoring 110. The processor may output feedback 108 per the daily cumulative risk determination 112. Further, in some embodiments, the continuous time series of risk values may be used to calculate a cumulative risk score 113 which may then be compared to a cumulative risk threshold as will be discussed further below.

While generally illustrated with orientation monitoring algorithms, activity monitoring algorithms, daily risk algorithms, and cumulative risk algorithms, it should be understood that embodiments may have one, some, or all of the functionality described above. Many embodiments may implement all of the functions, but other embodiments may be configured to only monitor user activity risk or only monitor orientation risks or other sub combinations of functions.

As discussed above, the sensor data received 102 may include force data and orientation data. The force data may be $F_x$, $F_y$, $F_z$ force data. In some embodiments, the force data may be used to determine when the user is engaged in significant activity and for how long the user is engaged in significant activity. The force data may also be used to identify activity risk values to provide a cumulative activity risk over a period of time.

Figure 9:
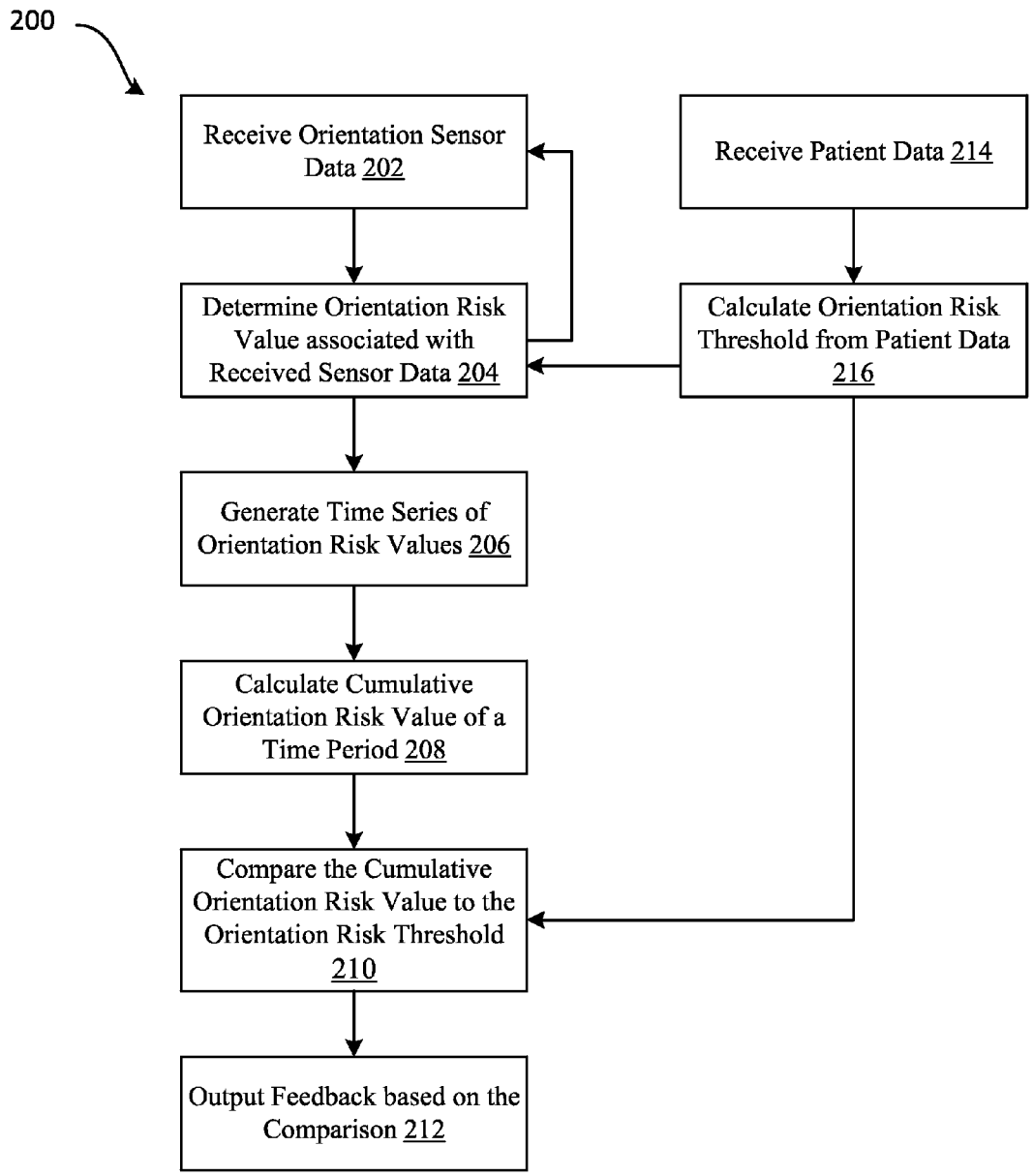
FIG. 9 illustrates an exemplary method for monitor orientation risks.

FIG. 9 illustrates an exemplary method 200 for monitor orientation risks 110. As mentioned above, it may be preferable to monitor user orientation only when it is determined that the user is not engaged in significant activity. At step 202, orientation sensor data is received. Based on the received orientation sensor data, a determination of an orientation risk value can be made 204. Steps 202 and 204 may be repeated for a continuous stream of orientation sensor data to generate a time series of orientation risk values 206. From the time series of orientation risk values, a cumulative orientation risk value may be calculated 208. The cumulative orientation risk value may then be compared to an orientation risk threshold 210. Feedback may then be outputted to the user 212 based on the comparison of the cumulative orientation risk value to the orientation risk threshold. Optionally, the method 200 may further include receiving patient data 214. An orientation risk threshold may be calculated or adjusted in response to the received patient data 216 to provide a customized orientation risk threshold. This customized orientation risk threshold may be used in the comparison 212.

The orientation data may be a recline angle (A) and a side tilt angle (φ). Each combination of θ and φ may correspond to an "Instant Position Risk Score." For example, this score may range from 0-1 (or scales thereof) where 1 may be indicative of the most dangerous orientation. Continuing with the exemplary scale, in some embodiments, oriented face down (while not lying on the stomach) may be valued at 0-0.05, preferably about 0.03; leaning forward at 45 degrees may be valued at 0.05-0.10, preferably about 0.08; standing straight up may be valued at 0.08-0.12, preferably about 0.10; leaning back at 45 degrees may be valued at 0.35-0.45, preferably about 0.4; and lying on back may be valued at 1.0. FIG. 10A illustrates exemplary orientation risk values for combinations of phi and theta. These orientation risk values may be stored as a look up table and accessed by the processor to associate orientation risk values to received orientation data. Alternatively, the processor may implement orientation risk value equations to calculate the orientation risk values.

For example, in the illustrated table of orientation risk values, six constants are provided: risk value for laying on the left side ("left side risk" i.e., when phi is equal to −90 degrees), risk value for laying on the right side ("right side risk" i.e., when phi is equal to 90), risk value for a headstand ("headstand risk" i.e., when theta is 180 or −180 and phi is 0), risk value for flat on stomach ("on stomach risk" i.e., when theta is −90 and phi is 0), the risk values for reclining by more than −90 degrees when not tilted sideways ("recline by more than −90 risk" i.e. when theta is between −90 and −180 and phi is 0), and risk value for standing upright ("standing risk" i.e., when theta is 0 and phi is 0). These constants may be defined by a clinician and may be adjusted for fine tuning the orientation risk values in the matrix (e.g., to provide customized risk values specific for the patient). The remaining risk values may be determined based on the six defined constants.

In the exemplary matrix the six constants may be defined as follows:

$risk_{left\ side}=0$ $risk_{right\ side}=0.3$ $risk_{headstand}=1.0$ $risk_{stomach}=0.01$ $risk_{-90<recline<-180}=1.0$ $risk_{standing}=0.1$ These constant values are exemplary for monitoring preeclampsia and may be adjusted.

In the illustrated table, when the user is reclined backward by between −90 and −180 degrees (−90>theta>−180) and tilted to the left (phi is between 0 and −90), the risk value may be calculated by:

$$risk = risk_{left\ side} + (1 - risk_{left\ side}) * risk_{-90<recline<-180} * \sqrt{1 + \sin(\frac{\pi\varphi}{180})}$$

When the user is reclined backward between 0 and −90 degrees or −90 degrees (i.e., 0<theta≤−90), and tilted to the left (phi is between 0 and −90), the risk value may be calculated by:

$$risk = risk_{left\ side} + (1 - risk_{left\ side}) *$$

$$\left(risk_{standing} + (1 - risk_{standing}) * \left(1 - \cos(\frac{\pi\theta}{180})\right)\right) * \sqrt{1 + \sin(\frac{\pi\varphi}{180})}$$

Further, when the user is recline backward or flat on his/her back (i.e., 0<theta≤−90 and phi is 0), the risk value may be calculated by:

$$\text{risk} = \text{risk}_{standing} + (1 - \text{risk}_{standing}) * \left(1 - \cos\left(\frac{\pi\theta}{180}\right)\right)$$

When the user is not reclined or leaning forward (i.e., theta is 0) and is tilted to the left (phi between 0 and −90 degrees), the risk value may be calculated by:

$$\text{risk} = \text{risk}_{standing} * \left(\text{risk}_{left\,side} + (1 - \text{risk}_{left\,side}) * \right.$$
$$\left. \left(\text{risk}_{standing} + (1 - \text{risk}_{standing}) * \left(1 - \cos\left(\frac{\pi\theta}{180}\right)\right)\right) * \sqrt{1 + \sin\left(\frac{\pi\varphi}{180}\right)}\right)$$

When the user is leaning forward but not inverted (i.e. 0<theta<90) and phi is 0, the risk value may be calculated by:

$$\text{risk} = (\text{risk}_{stomach} - \text{risk}_{standing}) * \cos\left(\frac{-\pi\theta}{180}\right)$$

When the user is leaning forward but not inverted (i.e. 0<theta<90) and tilted to the left (phi is between 0 and −90), the risk value may be calculated by:

$$\text{risk} = \text{risk}_{left\,side} +$$
$$(1 - \text{risk}_{left\,side}) * \left((\text{risk}_{stomach} - \text{risk}_{standing}) * \cos\left(\frac{-\pi\theta}{180}\right)\right) * \left(1 + \sin\left(\frac{\pi\varphi}{180}\right)\right)$$

When the user is leaning forward by more than 90 degrees (i.e., 180>theta>90) and phi is 0, the risk value may be calculated by:

$$\text{risk} = \text{risk}_{stomach} + (\text{risk}_{headstand} - \text{risk}_{stomach}) * \left(-\cos\frac{\pi\theta}{180}\right) * \text{risk}_{headstand}$$

When the user is flat on their stomach (theta=90) and tilting to the left (0>phi>−90), the risk value may be calculated by:

$$\text{risk} = \text{risk}_{left\,side} + (1 - \text{risk}_{left\,side}) * \text{risk}_{stomach} * \left(1 + \sin\left(\frac{\pi\varphi}{180}\right)\right)$$

When the user is leaning forward by more than 90 degrees (i.e., 180≥theta>90) and tilted to the left (0>phi>−90), the risk value may be calculated by:

$$\text{risk} = \text{risk}_{left\,side} + (1 - \text{risk}_{left\,side}) *$$
$$\left(\text{risk}_{stomach} + (\text{risk}_{headstand} - \text{risk}_{stomach}) * \left(-\cos\frac{\pi\theta}{180}\right) * \text{risk}_{headstand}\right) *$$
$$\sqrt{1 + \sin\left(\frac{\pi\varphi}{180}\right)}$$

When the user is tilting to the right side (0>phi>90), the risk value may be the risk value at an equivalent position when tilting to the left (risk$_{left\,equivalent}$) that factors in the right side risk. For example, in the illustrated matrix, when the user is tilting to the right side (0>phi>90), the risk may be calculated by:

$$\text{risk} = \text{risk}_{left\,equivalent} + \sin\left(\frac{\pi\varphi}{180}\right)^2 * \text{risk}_{right\,side}$$

Thus, when the user is reclined backward by between −90 and −180 degrees (−90>theta>−180) and tilted to the right (0>phi>90), the risk value may be calculated by:

$$\text{risk} = \left(\text{risk}_{left\,side} + (1 - \text{risk}_{left\,side}) * \text{risk}_{-90<recline<-180} * \sqrt{1 + \sin\left(\frac{\pi\varphi}{180}\right)}\right) +$$
$$\sin\left(\frac{\pi\varphi}{180}\right)^2 * \text{risk}_{right\,side}$$

When the user is reclined backward between 0 and −90 degrees or −90 degrees (i.e., 0<theta≤−90), and tilted to the right (0>phi>90), the risk value may be calculated by:

$$\text{risk} = \left(\text{risk}_{left\,side} + \right.$$
$$(1 - \text{risk}_{left\,side}) * \left(\text{risk}_{standing} + (1 - \text{risk}_{standing}) * \left(1 - \cos\left(\frac{\pi\theta}{180}\right)\right)\right) *$$
$$\left.\sqrt{1 + \sin\left(\frac{\pi\varphi}{180}\right)}\right) + \sin\left(\frac{\pi\varphi}{180}\right)^2 * \text{risk}_{right\,side}$$

When the user is not reclined or leaning forward (i.e., theta is 0) and is tilted to the right (0>phi>90), the risk value may be calculated by:

$$\text{risk} = \left(\text{risk}_{standing} * \left(\text{risk}_{left\,side} + \right.\right.$$
$$(1 - \text{risk}_{left\,side}) * \left(\text{risk}_{standing} + (1 - \text{risk}_{standing}) * \left(1 - \cos\left(\frac{\pi\theta}{180}\right)\right)\right) *$$
$$\left.\left.\sqrt{1 + \sin\left(\frac{\pi\varphi}{180}\right)}\right)\right) + \sin\left(\frac{\pi\varphi}{180}\right)^2 * \text{risk}_{right\,side}$$

When the user is leaning forward but not inverted (i.e. 0<theta<90) and tilted to the right (0>phi>90), the risk value may be calculated by:

$$\text{risk} = \left(\text{risk}_{left\,side} + (1 - \text{risk}_{left\,side}) * \left((\text{risk}_{stomach} - \text{risk}_{standing}) * \cos\left(\frac{-\pi\theta}{180}\right)\right) +$$
$$\left(1 + \sin\left(\frac{\pi\varphi}{180}\right)\right)\right) + \sin\left(\frac{\pi\varphi}{180}\right)^2 * \text{risk}_{right\,side}$$

When the user is flat on their stomach (theta=90) and tilting to the right (0>phi>90), the risk value may be calculated by:

$$\text{risk} = \left(\text{risk}_{left\,side} + (1 - \text{risk}_{left\,side}) * \text{risk}_{stomach} * \left(1 + \sin\left(\frac{\pi\varphi}{180}\right)\right)\right) +$$
$$\sin\left(\frac{\pi\varphi}{180}\right)^2 * \text{risk}_{right\,side}$$

When the user is leaning forward by more than 90 degrees (i.e., 180≥theta>90) and tilting to the right (0>phi>90), the risk value may be calculated by:

$$risk = \left( risk_{left\,side} + (1 - risk_{left\,side}) * \left( risk_{stomach} + (risk_{headstand} - risk_{stomach}) * \left( -\cos\frac{\pi\theta}{180} \right) * risk_{headstand} \right) * \sqrt{1 + \sin\left(\frac{\pi\varphi}{180}\right)} \right) + \sin\left(\frac{\pi\varphi}{180}\right)^2 * risk_{right\,side}$$

While these exemplary functions, constants, and constant values are provided, it should be understood that embodiments of the invention are in no way limited to the above functions and the exemplary constants or the exemplary constant values. As stated, the orientation risk values and equations may be customized or refined upon further clinical analysis. Optionally, as discussed above, look up tables may be used to associate risk values with orientation data. Additionally, it should be understood that other risk scales may be used. The exemplary 0-1 scale is provided for example only and is non-limiting.

Thus, based on the received orientation sensor data, a determination of an orientation risk value can be made 204. A time series of orientation risk values 206 may be determined as the sensor data is received. From the time series of orientation risk values, a cumulative orientation risk value may be calculated 208. The cumulative orientation risk value may be a moving average of the risk scores. For example, the cumulative orientation risk value may be the average of a subset of the time series of orientation risk values (e.g., the last 30 seconds—the last 1000 seconds of orientation risk values). In a preferred embodiment, the cumulative orientation risk value may be the average of the last 300 seconds of orientation risk scores. As the device receives the newest orientation risk score, it may discard the oldest, so that the most recent 300 seconds worth of orientation risk scores are always averaged to into the cumulative orientation risk value.

The cumulative orientation risk value may then be compared to an orientation risk threshold 210. In some embodiments, the orientation risk value may be compared to a first threshold and a second threshold. The first threshold may be a medium risk threshold and the second threshold may be a high risk threshold. For example, in some embodiments, the medium risk threshold may be between 0.15-0.25, preferably 0.2, and the high risk threshold may be between 0.35-0.45, preferably 0.4.

Feedback may then be outputted to the user 212 based on the comparison of the cumulative orientation risk value to the orientation risk threshold. For example, whenever the cumulative orientation risk value rises above the medium risk threshold, the device may deliver a first feedback and whenever the cumulative orientation risk value rises above the high risk threshold, the device may deliver a second feedback. The feedback may be audio, visual, or haptic. In some embodiments, when the cumulative orientation risk value rises above the medium risk threshold, the device may vibrate, beep, or flash once every two minutes until the cumulative orientation risk value improves and drops below the threshold. If the cumulative orientation risk value rises above the high risk threshold, the device may vibrate, beep, or flash twice every thirty seconds until the cumulative orientation risk score drops below the high risk threshold. The device may provide no feedback when the cumulative orientation risk score is below the medium and high thresholds. Optionally, the device may provide a visual feedback when the cumulative orientation risk score is below the medium and high thresholds (e.g., a green indicator or the like).

In some embodiments, the feedback may be a visual or audio feedback that suggests to the user to change to a more preferable orientation. For example, if a user is reclining on their back, an audio or visual feedback may suggest that they sit more upright, or lean to their side or the like.

The described feedback and thresholds are exemplary. It should be understood that the feedback alerts may have any number of configurations and may be customized by a clinician or a user.

Further, the method 200 may further include receiving patient data 214 to adjust or calculate one or more orientation risk thresholds 216. For example, user attributes or pregnancy factors may increase or decrease orientation risks. Preexisting hypertension, multiple pregnancy, user diabetes, body mass index, gestational age, may increase the risk associated with undesirable orientations. Accordingly, these factors may be taken into account by adjusting the orientation risk threshold value(s). This customized orientation risk threshold may be used in the comparison 212. This aspect is discussed further below.

Optionally, the factors may be taken into account by adjusting one or more of the risk constants in the orientation risk algorithm. For example, FIG. 10B illustrates an alternative adjusted or customized preeclampsia matrix of orientation risk values for users with incompetent cervix. In the exemplary matrix in FIG. 10B uses the same underlying functions of FIG. 10A, but one or more of the six risk constants may be adjusted. Cervical incompetence is a medical condition in which a pregnant woman's cervix begins to dilate and efface before her pregnancy has reached term. Accordingly, it may be beneficial for persons diagnosed with incompetent cervix to limit the amount of standing. Thus, the standing upright risk constant may be adjusted higher (e.g., to 0.5) compared to the standing upright risk constant of FIG. 10A to adjust or customize the matrix of risk values specific to the needs of the user.

Further, in some embodiments, the risk values or risk thresholds may be adjusted based on a gestational age of the user. For example, a position risk coefficient for gestational age may be provided. For example, the position risk algorithm may be adjusted to factor in a gestation age. For pregnant users, different positions may become riskier the later in gestation, so the following formula may be used for calculating a position risk coefficient to generate a gestational age modified instant activity risk score (gam.inst.risk.act) (or a modify an associated threshold), where gestational age is in weeks.

$$\text{Position Risk Coefficient}_{gest.age} = \frac{\tanh\left(\frac{gest.age - 10}{5}\right)}{2} + 0.5$$

Figure 16:
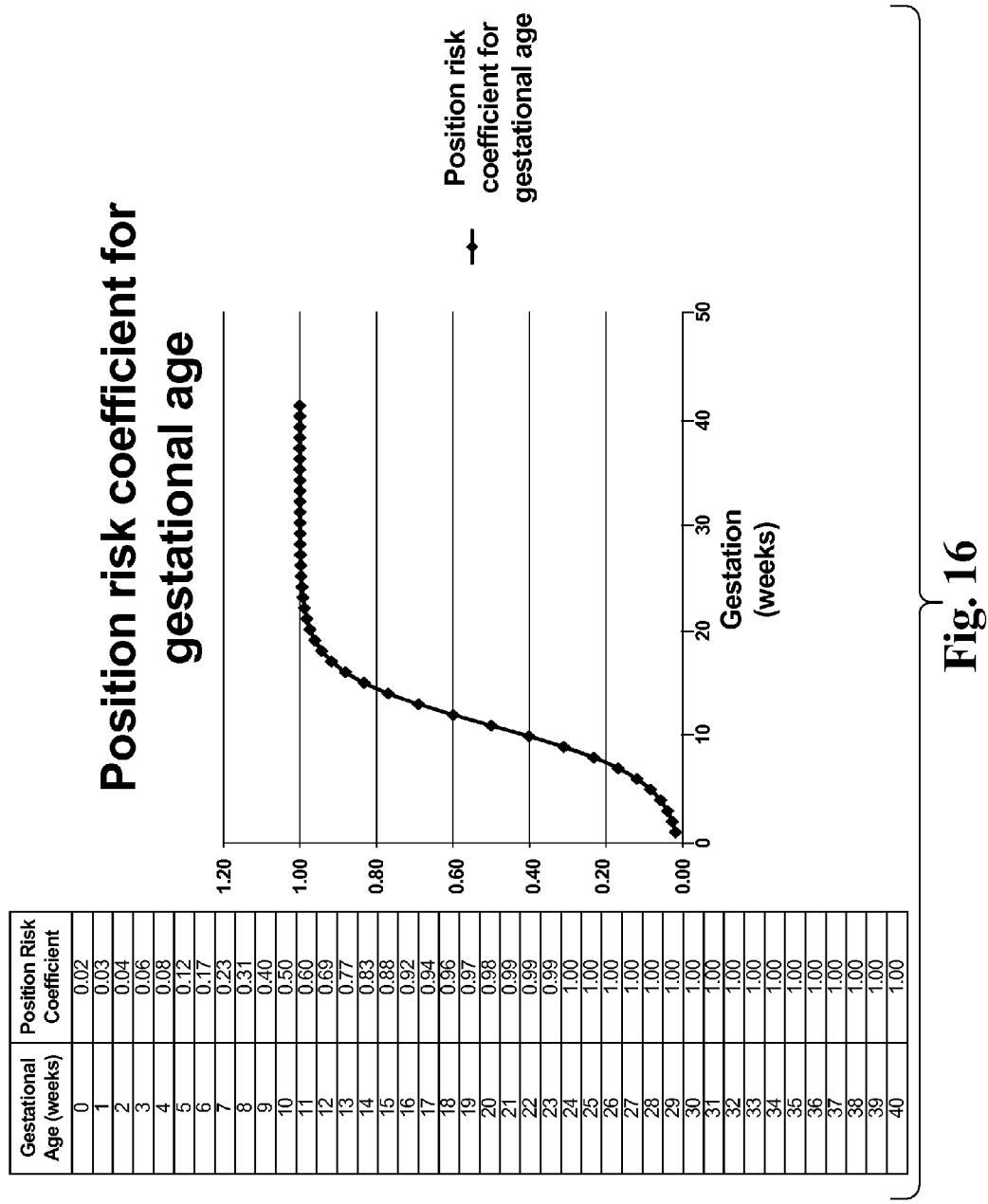
FIG. 16 illustrates a table and plot illustrating the exemplary relationship between risk coefficients and gestational age.

FIG. 16 illustrates a table and plot showing the exemplary relationship between risk coefficients and gestational age. This gestational age modifier algorithm is exemplary. As this is only applicable to pregnant users, this modifier may be turned off or on by the user. Other factors may be weighed as such as obesity, diabetes, multiple pregnancy, blood pressure, body mass index, etc. Other factors that may affect the threshold risk value are discussed further below.

Figure 11:
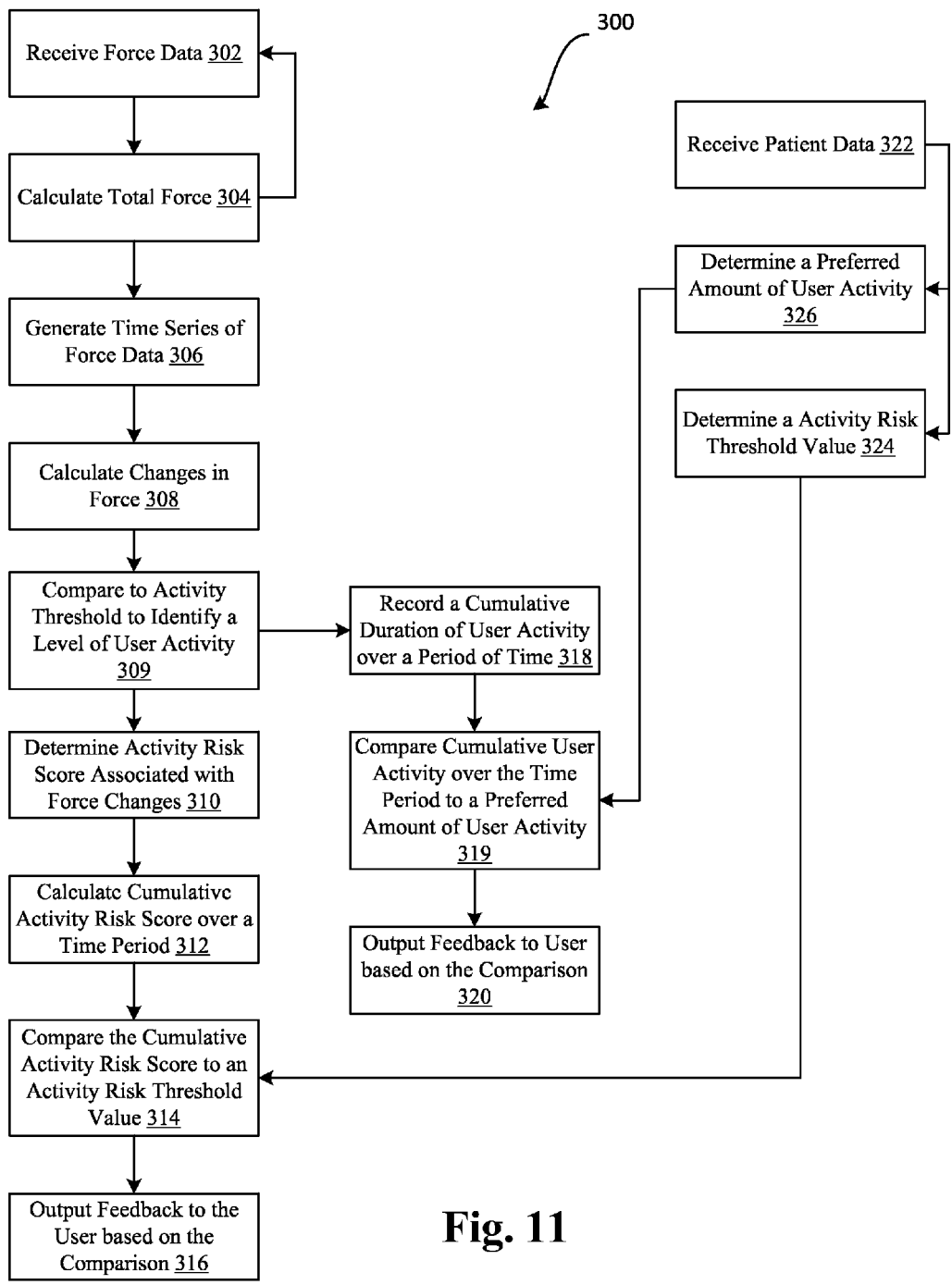
FIG. 11 illustrates an exemplary method for monitoring activity risks.

FIG. 11 illustrates an exemplary method 300 for monitoring activity risks. At step 302 force data is received. The total force experienced by the user may be determined from the received force data 304. A time series of force data may be generated 306. Changes in force may be determined using the time series of force data 308. The changes in force may be compared to an activity threshold to determine whether the user is engaged in a clinically significant level of activity 309.

To monitor activity risks, an activity risk score may be associated with the calculated force changes 310. A cumulative activity risk score may be calculated 312. The cumulative activity risk score may be compared to an activity risk threshold value 314. Based on the comparison, a feedback may be outputted to the user 316.

Additionally, a duration of the user activity may be recorded for a period of time 318. A cumulative duration of the user activity over the entire time period may be compared to a preferred amount of user activity 319. Based on the comparison, a feedback may be outputted to the user 320.

Similar to the orientation monitoring method described above, patient data may be received 322 and the user data may be used to adjust or calculate the activity risk threshold value 324. Further, the user data may be used to adjust or calculate the preferred amount of user activity 326. The customized activity risk threshold value 324 may be fed into step 314 for comparison to the cumulative activity risk score. The customized preferred amount of user activity 326 may be fed into step 319 for comparison to the cumulative user activity over the time period.

In some embodiments, the activity risk may be evaluated based on vigorousness rather than by activity type. Vigorousness may be depended on the delta in g-force at any point in time. As discussed above, the received force data may be $F_x$, $F_y$, $F_z$ force data. In some embodiments, the force data may be received at a frequency between 0.5-50 Hz and the received data may be placed into memory for further analysis. Preferably, the data is received at least at a frequency of 10 Hz. The total force experienced by the user may be determined from the received force data 304 by adding the absolute values of $F_x$, $F_y$, and $F_z$ to generate total g-force.

A time series of force data may be generated 306 and changes in force may be determined using the time series of force data 308. For example, a subset of the time series of force data may be defined and the minimum and maximum values may be extracted from the subset to calculate the force change. For example, a subset may include increments of 15 force values.

The changes in force may then be compared to an activity threshold to determine whether the user is engaged in a clinically significant level of activity 309. In embodiments where the force data is received every 0.1 seconds, the force change may be calculated every 1.5 seconds to determine if activity is still occurring and if so, what level of vigorousness. The average g-force when not moving will be −1. For the exemplary algorithm, if the total g-force regularly fluctuates from 0.75 to about 1.25 (or a delta of 0.5), over any 1.5 second span, the algorithm may determine that the user is engaged in clinically significant activity. In some embodiments, a number of thresholds may be used to identify different levels of activity. For example, when force changes=0-0.3, the algorithm may determine that the user is not engaged in activity. When the force changes=0.3-0.75, the algorithm may determine that the user is engaged in low activity. When the force changes=0.75-1.25, the algorithm may determine that the user is engaged in medium activity. When the force changes=1.25-2, the algorithm may determine that the user is engaged in high activity. When the force changes >2, the algorithm may determine that the user is engaged in dangerous activity. These values for vigorousness levels are exemplary.

A meter may be provided on the device, on a display of the device, or to a display of a coupled mobile device. The meter may indicate the activity level by taking a moving average of a subset of readings (e.g., the last two readings or the last three seconds of readings). This may provide a more fluid activity meter. Optionally, a rate of change for the activity meter may have an upper limit and a lower limit to limit the extreme changes in the activity meter and to provide a more fluid activity meter reading.

To monitor activity risks, an activity risk score may be associated with the calculated force changes 310. An example activity risk algorithm may provide a relatively low risk at low force changes (e.g., g-force change <0.5) but may then sharply increase and as force changes grows to 2 and higher the activity risk score may asymptote to 1. An exemplary activity risk algorithm may be:

$$\text{activity risk} = \frac{-0.5}{(\Delta \text{force} + 0.1)^{1.25}} + 1$$

This activity risk algorithm is exemplary and non-limiting.

A cumulative activity risk score may be calculated 312. The cumulative activity risk value may be a moving average of the risk scores. For example, the cumulative activity risk value may be the average of a subset of the time series of activity risk values (e.g., the last 30 seconds—the last 1000 seconds of activity risk values). In a preferred embodiment, the cumulative activity risk value may be the average of the last 300 seconds of activity risk scores. As the device receives the newest activity risk score, it may discard the oldest, so that the most recent 300 seconds worth of activity risk scores are always averaged to into the cumulative activity risk value.

The cumulative activity risk score may be compared to an activity risk threshold value 314. In some embodiments, the activity risk value may be compared to a first threshold and a second threshold. The first threshold may be a medium risk threshold and the second threshold may be a high risk threshold. For example, in some embodiments, the medium risk threshold may be between 0.15-0.25, preferably 0.2, and the high risk threshold may be between 0.35-0.45, preferably 0.4.

Based on the comparison, a feedback may be outputted to the user 316. For example, whenever the cumulative activity risk value rises above the medium risk threshold, the device may deliver a first feedback and whenever the cumulative activity risk value rises above the high risk threshold, the device may deliver a second feedback. The feedback may be audio, visual, or haptic. In some embodiments, when the cumulative activity risk value rises above the medium risk threshold, the device may vibrate, beep, or flash once every two minutes until the cumulative activity risk value improves and drops below the threshold. If the cumulative activity risk value rises above the high risk threshold, the device may vibrate, beep, or flash twice every thirty seconds until the cumulative activity risk score drops below the high risk threshold. The device may provide no feedback when the cumulative activity risk score is below the medium and high thresholds. Optionally, the device may provide a visual feedback when the cumulative activity risk score is below the medium and high thresholds (e.g., a green indicator or the like).

The duration of the user activity may be recorded for a time period 318. The time period may be a day, two days, a week, two weeks or the like. In some embodiments, it may be preferable to record a cumulative duration of user activity over the course of a week. The cumulative duration of the user activity over the entire time period may be compared to a preferred amount of user activity 319. Based on the comparison, a feedback may be outputted to the user 320.

In some embodiments, patient data may be received 322 and the user data may be used to adjust or calculate the activity risk threshold value 324 or to adjust an instant activity risk score. For example, the activity risk algorithm may be adjusted to factor in a gestation age. For pregnant users, exercise may become riskier the later in gestation, so the following formula may be used for calculating an activity risk coefficient to generate a gestational age modified instant activity risk score (gam.inst.risk.act), where gestational age is in weeks.

$$gam.inst.risk.act = \frac{\tanh\left(\frac{gest.age - 20}{5}\right)}{2} + 0.5$$

This gestational age modifier algorithm is exemplary. As this is only applicable to pregnant users, this modifier may be turned off or on by the user. Other factors may be weighed as such as obesity, diabetes, multiple pregnancy, blood pressure, body mass index, etc. Other factors that may affect the threshold risk value are discussed further below.

Further, the user data may be used to adjust or calculate the preferred amount of user activity 326. For example, in some embodiments where the device is used to monitor pregnant user activity, an age of gestation may be factored in to calculate or determine the preferred amount of user activity. For example, early pregnancy (e.g., before 20 weeks of gestation) may have a different preferred amount of user activity compared to a preferred amount of user activity during late pregnancy (e.g., after 30 weeks of gestation). In some embodiments, 4 hours or less of intense physical activity per week before 20 weeks may be recommended. Additionally, 2 hours or less of intense physical activity per week may be recommended for pregnant women between 21-30 weeks. After 30 weeks, the device may be configured to discourage any intense activity.

In some embodiments, the algorithm may discourage long durations of moderate activities and short durations of vigorous activities. In some embodiments, the feedback may be configured to encourage certain low level activities like slow walking and may discourage more vigorous ones like running. Advantageously, the activity monitor may remind patients to take breaks throughout the day based on a schedule and/or based on the level of activity experienced to that point that day.

Optionally, the algorithm may have set adjustments to conform to levels of bed rest. For example, the algorithm may be preprogrammed to be switchable between modified activity monitoring, scheduled rest monitoring, bed rest monitoring, and/or hospital bed rest. In some embodiments, the algorithm may be configured to estimate blood pressure in the abdomen or other parts of the body based on a level of activity for a set duration of time (e.g., three minutes or the like). In some embodiments, the device may estimate blood pressure as a function of recent user activity and orientation of the body as a whole. Optionally, the device may estimate blood pressure as a function of the orientation of the abdomen relative to the IVC. This blood pressure estimate may be feedback into the overall algorithm where the higher the blood pressure, the lower the thresholds.

In some embodiments, the time series of orientation risk scores may be combined with the time series of activity risk scores to generate a continuous time series of risk values 111. For many embodiments, the device may generate either an activity risk score or an orientation risk score throughout the day (e.g., every second or more) to provide a continuous series of activity and orientation risk scores.

This time series of risk scores may then be used to calculate a cumulative daily risk score 112. For example, in some embodiments, the daily score may start at 100 and drop by an amount equal to $1/(60\ s*60\ min*Hours_{day})$ *100*"instant risk score" every second of the day. The cumulative daily risk score equation is exemplary and non-limiting. The equation may be tuned to revise/update the cumulative daily score more frequently (e.g., every tenth of a second, every half a second, etc.) or less frequently (e.g., every two seconds, every five seconds, etc.).

The $Hours_{day}$ variable is the time duration over which the cumulative daily score is calculated. In some embodiments, the $Hours_{day}$ variable may be between 14-24 hrs, preferably 24 hrs. When the 24 hr duration is used, the device may be programmed to start recording the cumulative daily risk value at 1:00-5:00 AM in the time zone of the user.

After the cumulative daily health score is calculated, the score may be compared to a daily risk threshold. In some embodiments, a low risk patient may aim to stay above 80, a higher risk patient may aim to stay above 90 and a patient prescribed bed rest (for example) may aim to stay above 95. These thresholds are exemplary and non-limiting. In many embodiments the daily risk thresholds may be raised or lowered or otherwise customized for a user based on user factors.

The continuous time series of risk scores may also be used to calculate a combined moving average risk score 113. Similar to the other cumulative risk scores, the combined moving average risk value may be the average of a subset of the continuous time series of activity risk values and orientation risk values combined (e.g., the last 30 seconds—the last 1000 seconds of activity risk values). In a preferred embodiment, the combined moving average risk value may be the average of the last 300 seconds of activity risk scores and orientation risk scores. As the device receives the newest activity risk score or orientation risk score, it may discard the oldest score, so that the most recent 300 seconds worth of activity risk scores and/or orientation risk scores are always averaged to into the combined moving average risk value.

The combined moving average risk score may be compared to a combined moving average risk threshold value. In some embodiments, the combined moving average risk value may be compared to a first threshold and a second threshold. The first threshold may be a medium risk threshold and the second threshold may be a high risk threshold. For example, in some embodiments, the medium risk threshold may be between 0.15-0.25, preferably 0.2, and the high risk threshold may be between 0.35-0.45, preferably 0.4.

Based on the comparison, a feedback may be outputted to the user. For example, whenever the combined moving average risk value rises above the medium risk threshold, the device may deliver a first feedback and whenever the combined moving average risk value rises above the high risk threshold, the device may deliver a second feedback. The feedback may be audio, visual, or haptic. In some embodiments, when the combined moving average risk value rises above the medium risk threshold, the device may vibrate, beep, or flash once every two minutes until the combined moving average risk value improves and drops below the threshold. If the combined moving average risk value rises above the high risk threshold, the device may vibrate, beep, or flash twice every thirty seconds until the combined moving average risk score drops below the high risk threshold. The device may provide no feedback when combined moving average risk score is below the medium and high thresholds. Optionally, the device may provide a visual feedback when the combined moving average risk score is below the medium and high thresholds (e.g., a green indicator or the like).

When monitoring the orientation, activity, or a combination of the two, the device may utilize multiple cumulative orientation risk values, cumulative activity risk values and/or combined moving average risk values. Accordingly, in some embodiments, the device may calculate two, three, four, or more cumulative orientation risk values and may separately calculate two, three, four, or more cumulative activity risk values. Similarly, two, three, four, or more combined moving averages may be calculated. For example, the device may employ cumulative scores over multiple lengths of time (e.g., last 2 minutes, last 5 minutes, last 15 minutes, etc.). Further each of the cumulative values may be associated with a different threshold clinical value tolerance before an alert is generated.

As discussed above and throughout, in many embodiments, the threshold values used in the orientation risk algorithm, the activity risk algorithm, and/or the cumulative daily risk algorithm may be raised or lowered and/or customized for users. These threshold values may be adjusted based on patient risk factors including, but not limited to multiple pregnancy (twins, triplets, etc.), obesity, hypertension, age of gestation, body mass index, etc.

For example, in many embodiments, the patient may input etiological info and the device and algorithm may be customized for them. For example, the device algorithm may monitors position and activity differently depending upon stage of pregnancy and risk level.

For example, the Overall Relative Etiological Risk (ore.risk) may be factored into the medium risk and high risk thresholds discussed above to change the threshold at which alarms are triggered. The ore.risk will typically be a value between ~0.5 and 10 where 0.5 is a very low risk patient, 1 is an average risk patient, and 10 is a very high risk patient.

So, the medium risk and high risk thresholds may be modified by the ore.risk value in order to create the new threshold alert levels. For example and etiological adjust medium risk may be calculated by:

eti.adj.med.risk=med.risk/sqrt(ore.risk)

For example, a Low risk patient may be skinny, with low blood pressure, and on her $2^{nd}$ pregnancy with an ore.risk score of 0.6.

$$eti.adj.med.risk = med.risk / sqrt(ore.risk) = \frac{.2}{.78} = .26$$

In a further example, a med (average) risk patient (thin, low blood pressure, $2^{nd}$ pregnancy) with an ore.risk score of 1.

$$eti.adj.med.risk = med.risk / sqrt(ore.risk) = \frac{.2}{1} = .2$$

In yet another example, High risk patient (thin, low blood pressure, $2^{nd}$ pregnancy) with an ore.risk score of 9.

$$eti.adj.med.risk = med.risk / sqrt(ore.risk) = \frac{.2}{3} = .7$$

As can be seen, the medium risk threshold for the alert to be triggered gets lower as the patient becomes increasingly likely to develop preeclampsia. This means they would be more frequently encouraged to lower their activity and remain in lower risk orientations.

The algorithm may take many other patient risk factors into consideration (twins, obesity, hypertension, age of gestation, etc.) to customize the alert threshold for each patient. The output of this risk etiological algorithm ranges between ~0.5 and ~10 where 10 is most likely to develop preeclampsia.

A $2^{nd}$ time mother who is thin and healthy might have a score of 0.7 whereas an obese first time mother with chronic hypertension might have a score of 5.0. The Overall Relative Etiological Risk (ore.risk) may be factored into the various risks calculated by the device. The ore.risk may be calculated my multiplying all the relative exemplary risks together in the exemplary table illustrated in FIG. 12. The list of factors is exemplary and further the proposed values are non-limiting. Table 1 illustrates a chart which may be used to inform the patient what their risk level is for preeclampsia.

| Low Risk | 0 to .8 | You have a preeclampsia risk less than the average woman |
| Medium Risk | .81 to 1.5 | You have an average risk of preeclampsia |
| High Risk | 1.51 to 3 | You have an elevated risk of preeclampsia |
| Very High Risk | 3.1 and higher | You have a very high risk of preeclampsia |

In many embodiments a user interface of the device may receive input from the user of these pregnancy factors. For example, a software may ask the user to input the maternal birth date. In response to the maternal birth date input, the device may be configured to take the current date and subtract the maternal birth date to determine maternal age. As discussed above, the maternal age may play a factor in the threshold calculations or customizations and the preferred amount of cumulative user activity during a time period.

Additionally, the user interface may request a height and weight of the user in order to calculate body mass index. For example, the weight may be received in pounds and the height received in feet and inches. The device may be configured to convert this input into BMI units of $kg/m^2$.

Further, the device may be configured to request a due date input. The software may calculate the current age of gestation (gest.age) in weeks. This may be used as a gestational risk factor.

In some embodiments, the system may include a blood pressure cuff which automatically syncs with the device software and records blood pressure readings. In some embodiments, the blood pressure cuff may wirelessly couple with the device. Additionally, or alternatively, the device may request patient blood pressure input. In some embodiments, the device may periodically request users to take their blood pressure at certain times for input into the device. The blood pressure readings then flow into the algorithm and the threshold levels may be adjusted accordingly (e.g., lowered for users with higher blood pressure).

In some embodiments, the system may include a blood oxygen level detector.

The blood oxygen level detector may either be 1) a separate attachment that goes over the finger, or 2) a light and detector that shines outward from the device which requires the user to put their finger on the device, or 3) it may be a portable electronics device (e.g., phone, PDA, tablet, etc.) application which requires the user to put their finger on the camera, or 4) it may be on the device and oriented towards the body for takes measurements from the chest or abdominal skin. Oxygen saturation can be measured by the device and the data may be used to alert the patient when they need to contact physician. For example, SpO2 of 90-93% increases risks over the next 48 hrs by 20× compared to SpO2 of 98-100%.

Device could include fetal heart rate monitor and uterine contraction detector (tocometer).

In some embodiments, the device could ask patient to measure their ankle diameter initially as a baseline and then throughout pregnancy to monitor preeclampsia risk.—The swelling of legs may be an important symptom of preeclampsia. Optionally, a self-measuring cuff (e.g. the Health-o-Meter digital tape measure) may be provided. In some embodiments, the measurement cuff could be integrated into blood pressure cuff. The ankle diameter data may be fed into the device algorithms and thresholds may be adjusted accordingly (e.g., swelling of the ankles results in lower threshold values).

In one embodiment, a tabletop or wall mounted device transmits and detects short radio waves (in one embodiment, 10 GHz) that bounce off the user. These radio waves transmit through fabric but are partially reflected by the body, thereby detecting orientation, motion and breathing patterns of the user. In a further embodiment, many of these devices are located throughout the user's home and are used to continually track user orientation, activity, and breathing characteristics.

In one embodiment, pulse wave transit time is used to estimate absolute blood pressure or blood pressure changes. In one embodiment, the chest strap of the device may include 2 electrodes, one on the left and one on the right side of the chest. The electrodes may transmit a current through the chest and measure impedance. This method (impedance phethysmography) is known to generate an ECG waveform. The device may simultaneously measure the user's finger or wrist pulse via pulse oximetry. The device may then combine the ECG data and extremity pulse rate to calculate pulse wave transit time which may be used to estimate blood pressure. In one embodiment, the pulse oximetry is performed by the camera or light sensor on a mobile phone or other mobile device that is wirelessly connected to the device. In another embodiment, the device has 2 electrodes which the user touches with fingers on opposite arms. One or more of these electrodes also has a camera or light sensor and light source to measure the pulse in the finger by pulse oximetry. In another embodiment, the electrodes in the strap contact the left and right sides of the chest to generate the ECG data and the user touches a light sensor or camera on the device with one or more fingers to generate the extremity pulse signal.

Optionally, when certain thresholds (orientation, activity, blood pressure, blood oxygen, etc.) are exceeded, the device may be configured to automatically alert a doctor or the patient is advised to call a doctor. Accordingly, some embodiments of the invention are diagnostic as well as therapeutic.

In one embodiment, the system includes a sensor located on the lower abdomen, legs, feet, or toes to determine when flow in the IVC and/or aorta may be compromised. In some embodiments, this sensor is a blood oxygen sensor, blood pressure sensor, or temperature sensor.

In some embodiments, the algorithm suggests specific maternal orientations that prevent breach orientation of the fetus or to help move a breach baby to another orientation.

In some embodiments, the device monitors respiration characteristics by using an accelerometer to calculate the deviation of the chest outward and inward. In another embodiment, the device uses tension sensors in the chest strap to calculate frequency and depth of breath. In some embodiments, this respiration data is used to determine whether the sleeping user is snoring, has sleep apnea, or has another breathing disorder. In some embodiments, the device vibrates to alert the patient if the sleep disordered breathing passes a specific threshold, an examples include having more than 2 pauses in breathing in a 10 minute period or snoring lasting longer than 1 minute. In further embodiments, the device may also have a microphone to determine is the user is snoring.

In some embodiments, the device may include a training system which teaches the patient which orientations or activities are considered risky. For example, in training mode, the device buzzes once when the patient enters a position of risk level 0.2 to 0.39, buzzes twice for risk level 0.4 to 0.59, buzzes 3 times for risk level 0.6 to 0.79, and buzzes continuously for risk level 0.8 to 1.

In some embodiments, the device may be configured to upload sensor data to a database for further analysis. The sensor data from a plurality of device may be gathered and the thresholds and algorithms may be further refined. Accordingly, in some embodiments, the system may become more accurate and precise over time as it collects patient data and refines the algorithms and threshold values. In some embodiments, the different positions may be subdivided into different groups for a regression analysis to compare time spent in each of those positions to age of gestation at birth.

Figures 12, 13, 14:
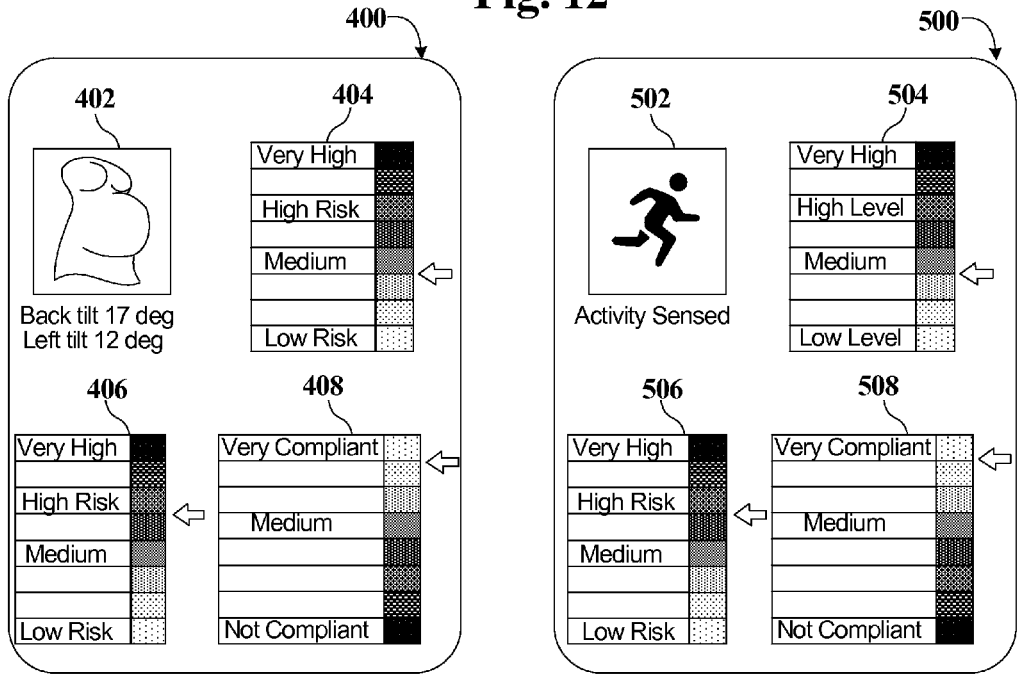
FIG. 12 shows exemplary risk factors and exemplary risk values for customizing an orientation and/or activity monitoring algorithm according to some embodiments.
FIG. 13 illustrates an exemplary user interface for orientation risk monitoring according to some embodiments.
FIG. 14 illustrates an exemplary user interface for activity risk monitoring.

FIG. 13 illustrates an exemplary user interface 400 for orientation risk monitoring according to some embodiments. User interface 400 may include a 3D CAD image 402. The 3D CAD image may constantly rotate to mirror the user's orientation. The user interface 400 may further include a real time position risk meter 404. A cumulative orientation risk value or a combined moving average risk meter 406 may also be displayed. A daily compliance meter 408 may also be provided. The daily compliance meter 408 may operate like a fuel-gauge—it may start at full and drop throughout the day.

When the device detects activity it may switch from the orientation user interface 400 to the activity monitoring user interface 500 illustrated in FIG. 14. Similarly, when the device ceases to detect activity, it may switch from the activity monitoring user interface 500 to the orientation monitoring user interface 400. Optionally, both interfaces 400, 500 may be displayed to the user with an indication as to which one is active or passive (e.g., highlighted, dimmed, etc.).

User interface 500 may illustrate an activity icon 502. The activity icon 502 may be representative of a running person. As activity score increases, the icon 502 may be displayed as running at a faster speed. The user interface 500 may further include a real time activity risk meter 504. Similar to user interface 400, user interface 500 may also include a cumulative activity risk meter or a combined moving average risk meter 506. The daily compliance meter 508 may also be provide on the user interface 500.

In some embodiments, the bottom two meters on user interface 400 and user interface 500 may be the same. In such configurations, the top half of the screen may automatically switch between activity 504 and position risk 404 meters depending upon whether or not activity is detected.

In a preferred, non-limiting embodiment, the device may provide some or all of the following menu hierarchy:

Patient Information
  Email
  Due date
  First name
  Last name
  Doctor email
  Maternal birth date
  Any prior live births? [y/n]
  Twins or more currently in utero? [y/n]
  Preexisting hypertension (high blood pressure)? [y/n]
  Height [feet and inches]
  Weight [lbs]
  Diabetes Mellitus? [y/n]
  Highest Maternal Education Level
    None
    Elementary
    Middle and/or high school
    College
  Currently living with baby's father [y/n]
  Previous Abortion [y/n]
  Cigarette smoking
    No
    1-9 cigarettes per day
    10 or more cigarettes per day
  Fetal malformation [y/n]
Training Mode
Share Data
  Email recipients:
  Email patient [checkbox](change patient email)
  Email doctor [checkbox] (change doctor email)
  Email other [enter email address]
  All Data [checkbox] or Date Range [enter 2 dates]
Contact BellyBit
  San Francisco, Calif. based BellyBit, Inc can be reached at [email address]
Advanced Options
  Modify algorithms by gestational age [on/off]
  Modify algorithms by etiological factors [on/off]
  Medium level alert [choose value 0 to 1 with 0.2 as default]
  High level alert [choose value 0 to 1 with 0.4 as default]
  Calibration sensitivity [choose value 0 to 1 with 0.02 as default]
  Temporary Risk Estimator [0 to 1; to 2 decimal places]
Calibrate Device The software may be configured to email the following sets of data on separate pages of an electronic spreadsheet document (such as, for example, an Excel® spreadsheet):

Total time app was used, % of time activity was sensed, and Daily Cumulative risk score [final score of the day; 1 data point per day for each of these 3 scores]

Daily cumulative risk score on a running basis [numerous points per day at 10 min intervals; e.g. a total of 60 points if device was used 10 hrs in one day]

Moving average risk score [data points at 2 min intervals; e.g., total of 300 data points for one 10 hour day]

Instant Position risk score and Instant Activity risk score [essentially, all the raw data at 1 sec intervals]

All days of data may be combined onto one page (workbook sheet) for each of the 4 data types for a total of 4 pages of data.

Figure 15:
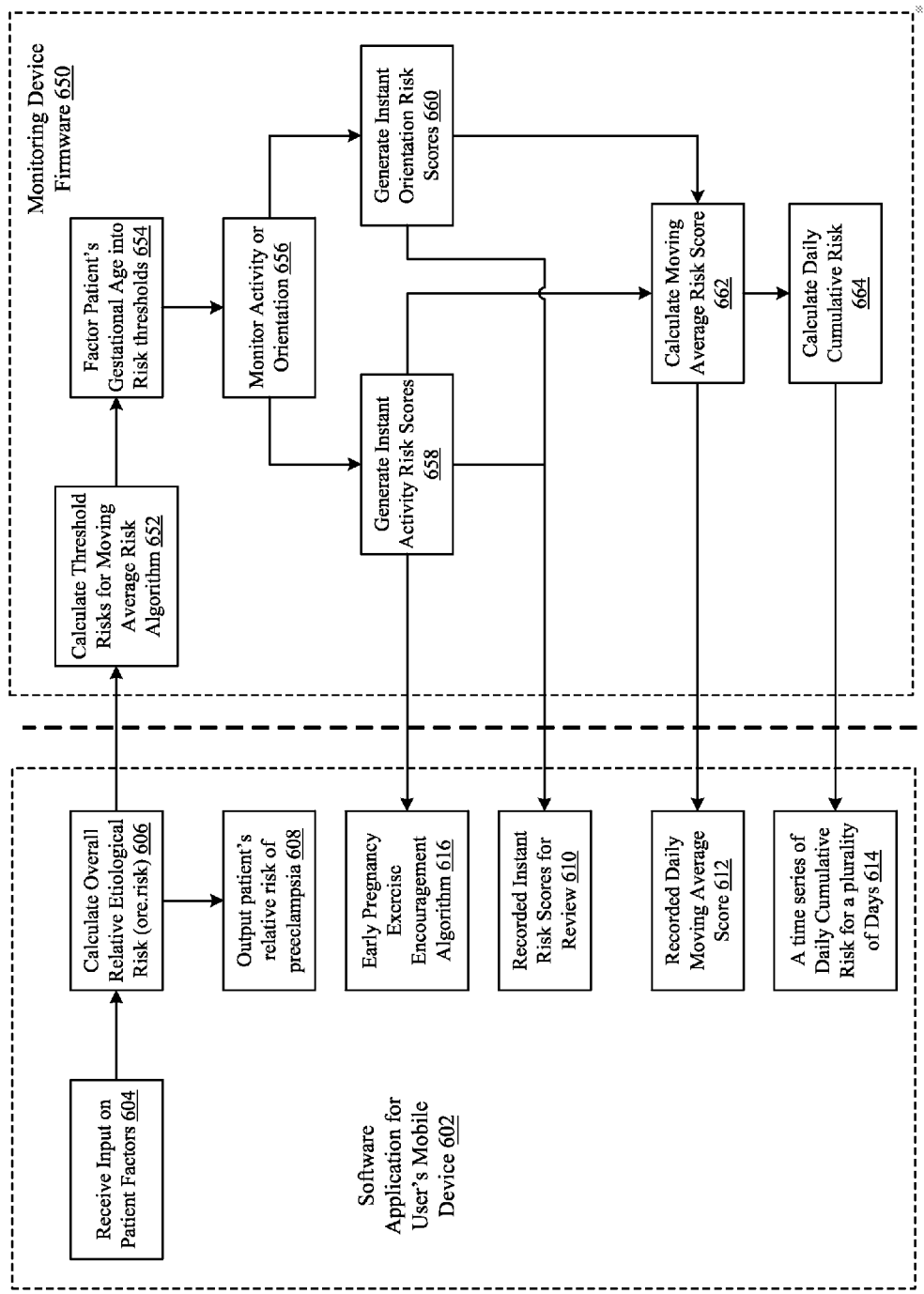
FIG. 15 illustrates another exemplary method according to some embodiments.

FIG. 15 illustrates another exemplary method and system 600 according to some embodiments. In the illustrated system 600, a software application 602 may be loaded onto the user's personal mobile device. The user's mobile device may be a portable electronics device such as, a smartphone, table computer, PDA, smartwatch, etc. The software application 602 may receive input on patient factors 604. The received factors may be one or more of the factors discussed above (e.g., maternal age, due date, height, weight, history of hypertension, etc.) The software application 602 may calculate overall relative etiological risk (ore.risk) 606 using the user inputted patient factors 604. The relative etiological risk (e.g., a value ranging from 0.5 to 10, for example) may be calculated from a formula in the software 602 that is based on regression analysis of known risk factors. The software application 602 may then output the user's relative risk of preeclampsia 608 (e.g., output to a display on the mobile device). The relative risk may be identified using the thresholds and categories in Table 1, for example.

Thereafter the software 602 may send the ore/risk to the monitoring device firmware 650. The device firmware 650 may revise default threshold values to factor in ore.risk 652 to provide the etiological adjusted medium risk and etiological adjusted high risk. For example, if med.risk=0.2; high.risk=0.4; and ore.risk=2.1 then:

$$\text{eti.adj.med.risk} = \text{med.risk}/\text{sqrt}(\text{ore.risk}) = 0.14$$

$$\text{eti.adj.high.risk} = \text{high.risk}/\text{sqrt}(\text{ore.risk}) = 0.28$$

Thereafter, a patient's gestation age (gest.age) may be factored into the risk thresholds 654. Continuing with the above example, if gest.age=27 (weeks), then:

$$gest.adj.med.risk = eti.adj.med.risk * \left( \frac{\text{TANH}\left(\frac{gest.age - 20}{5}\right)}{2} + 0.5 \right) = 0.13$$

The device firmware 650 may then monitor activity and/or orientation 656 using the customized thresholds. Instant activity risk scores may be produced 658. The instant activity risk scores may be associated with a vigorousness level of activity. Instant orientation risks cores may be produced 660. Often, the risk scores are produced to generate a time series of risk scores.

These risk scores may be combined and fed into the moving average risk score 662 where the algorithm calculates whether risk score is above the gest.adj.med.risk or gest.adj.high.risk thresholds and alerts the user as appropriate. Further a Daily Cumulative Risk may be calculated using the combined time series of risk scores 664.

Optionally, the instant activity and instant orientation risk scores may be transmitted back to the user's mobile device for storage and/or analysis 610. For example, the software application 602 may display a meter bar graph corresponding to the instant risk score. The meter bar graph may, for example, display the instant risk scores for the entire day averaged at one minute intervals. The software application 602 may also allow user may access this information to provide the user more detail about the instant risk score.

The moving average risk score may also be transmitted back to the user's mobile device for storage and/or analysis 612. The software 602 may allow the user to access this information to provide the user more detail about the moving average risk score. The software 620 may also be configured to display a bar graph corresponding to the moving average risk scores. For example, the bar graph may display all the moving average risk scores for the entire day averaged at one minute intervals.

The daily cumulative risk may also be transmitted back to the user's mobile device for storage and/or analysis 614. The software 602 may maintain a history of daily cumulative risk for all days. The software 602 may also be configured to display a bar graph with all the daily cumulative risk bars for all days of the pregnancy. A color of each bar may correspond to the level or risk.

Further, in some embodiments, the instant activity risk score may be transmitted to the user's mobile device for further analysis 616. For example, an early pregnancy exercise encouragement algorithm may be provided 616. For patients in their early stages of pregnancy (e.g., 15 weeks) a certain amount of vigorous activity may be beneficial and encouraged by the software 602. The preferred level of vigorous activity may trail off at 15 weeks and may get progressively more restrictive beyond 15 weeks. A meter may display the cumulative number of minutes of vigorous exercise each day with the target minutes listed as well.

In some embodiments, instant, average, daily, and other risk scores are calculated as or converted to "health scores." In some embodiments, a maximum risk score of 1 corresponds to a minimum health score of 0, and a minimum risk score of 0 corresponds to a maximum health score of 1.

While some embodiments are generally discussed in terms of monitoring orientation and activity of pregnant women, many methods, devices, and systems may be applied to any other area of the body where different positions have different levels of risk or benefit associated with them. For example, patients with obesity related hypertension may benefit from preventing abdominal fat from chronically or periodically compressing renal nerves and abdominal veins which may increase hypertension. In another example, in a patient with back pain, the algorithm assigns different levels of risk or detriment to different positions. The cumulative negative impact over time that the patient experiences while in various positions is added up and compared to allowable risk-time levels to determine whether the patient should be alerted to change position in order to prevent back pain or muscle or nerve inflammation. Devices and methods may be beneficial to patients suffering from gastroesophahael reflux or other digestive disorder that require they spend time in certain positions. Other diseases that may benefit from embodiments disclosed herein include Chorea, Parkinson's, and heart disease.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

In some embodiments, temperature of the user is measured in order to determine the ideal fertility window for conception. In further embodiments, an algorithm estimates how much the core temperature of the user has risen due to exercise or general activity. In some embodiments, the algorithm gets smarter over time by calibrating vigorousness of activity with temperature rise. In some embodiments, the temperature is measured directly by the device using sensors. In some embodiments, these sensors are on the skin, under the armpit, in the ear, intravaginal, or other places of the body known to provide consistent temperature measurements. In some embodiments, a temperature sensor worn on the outside of the body measures ambient air temperature and another sensor on the skin measures skin temperature. Further, in some embodiments, an algorithm account for the cooling or warming effect the environment has on skin temperature in order to estimate a more accurate body temperature.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A device for inhibiting preeclampsia in a woman, the device comprising:
   a. a sensor configured to generate orientation data;
   b. a support configured to couple the sensor to the torso of the woman such that the orientation data is indicative of an orientation of the abdomen; and
   c. a processor coupled to the sensor so as to receive the orientation data, the processor configured to calculate a time series of values in response to the data and a cumulative risk value in response to the values, the processor having an output for transmitting a warning in response to the risk value such that preeclampsia risk is mitigated.

2. The device of claim 1, further comprising a respiration sensor configured to generate respiration data of the user, the respiration sensor coupled with the processor, wherein the processor is configured to identify and assess risk associated with types of sleep disordered breathing based on the respiration data and output a warning when the risk level crosses a threshold.

3. The device of claim 1, wherein the processor is further configured to receive blood pressure data of the user, and wherein the processor raises or lowers the risk score in response to the received blood pressure data.

4. The device of claim 1, wherein the warning in response to the risk values is configured to include at least one additional risk notification selected from the group consisting of: hypertension, preterm birth, premature birth, intrauterine growth restriction (IUGR), stillbirth and small for gestational age (SGA).

5. The device of claim 1, further comprising at least one sensor in operational communication with the processor and configured to generate sleep data, wherein the processor raises or lowers the risk score in response to the received sleep data.

6. The device of claim 1, wherein the processor is configured to calculate a time series of sleep values in response to the sleep data and a cumulative sleep risk value in response to the sleep values, the processor having an output for transmitting a warning in response to the sleep risk value such that sleep disordered breathing risk is mitigated.

7. The device of claim 6, wherein sleep disordered breathing includes of at least one characteristic selected from the group consisting of: snoring, central sleep apnea and obstructive sleep apnea.

8. The device of claim 1, wherein the sensor configured to generate orientation data is also configured to generate respiration data.

9. The device of claim 8, wherein respiration data includes at least one measurement selected from the group consisting of: movement of chest, sound of snoring or gasping, electrical ECG signals and oxygen saturation.

10. A device for inhibiting preeclampsia in a woman, the device comprising:
   a. a sensor configured to generate orientation data; and
   b. a processor coupled to the sensor so as to receive the orientation data, the processor configured to calculate a time series of values in response to the data and a cumulative risk value in response to the values, the processor having an output for transmitting a warning in response to the risk value such that preeclampsia risk is mitigated,
   wherein the orientation data comprises a recline angle (pitch) and a sideways tilt angle (roll) and wherein the orientation risk values are a function of the recline angle and the sideways tilt angle.

11. The device of claim 10, further comprising a sensor configured to generate maternal respiration data.

12. The device of claim 11, wherein the processor is configured to calculate a time series of respiration values in response to the maternal respiration data and a cumulative risk value in response to the respiration values.

13. The device of claim 12, wherein respiration data includes at least one measurement selected from the group consisting of: movement of chest, sound of snoring or gasping, electrical ECG signals and oxygen saturation.

14. The device of claim 10, wherein the warning in response to the risk values is configured to include at least one additional risk notification selected from the group consisting of: hypertension, preterm birth, premature birth, intrauterine growth restriction (IUGR), stillbirth and small for gestational age (SGA).

15. A device for inhibiting pregnancy complications in a woman, the device comprising:
   a. a sensor configured to generate orientation data;
   b. a support configured to couple the sensor to the torso or abdomen of the woman such that the orientation data is indicative of an orientation of the abdomen; and
   c. a processor coupled to the sensor so as to receive the orientation data, the processor configured to calculate a time series of values in response to the data and a cumulative risk value in response to the values, the processor having an output for transmitting a warning in response to the risk value such that at least one pregnancy risk is mitigated.

16. The device of claim 15, wherein the pregnancy risk is selected from the group consisting of: hypertension risk, preterm birth risk, premature birth risk, intrauterine growth restriction (IUGR) risk and small for gestational age (SGA) risk.

17. The device of claim 15, further comprising a sensor configured to generate maternal respiration data.

* * * * *